(12) United States Patent
Ramanand et al.

(10) Patent No.: US 11,964,066 B2
(45) Date of Patent: Apr. 23, 2024

(54) UNIFIED AIRFLOW SYSTEM FOR ULTRAVIOLET DISINFECTION DEVICES

(71) Applicant: Angelica Holdings LLC, Dover, DE (US)

(72) Inventors: Prakash Valentino Ramanand, Burlington (CA); Manjinder Singh Dhillon, Milton (CA)

(73) Assignee: Angelica Holdings LLC., Dover, DE (US)

( * ) Notice: Subject to any disclaimer, the term of this patent is extended or adjusted under 35 U.S.C. 154(b) by 0 days.

(21) Appl. No.: 18/094,224

(22) Filed: Jan. 6, 2023

(65) Prior Publication Data

US 2023/0149576 A1    May 18, 2023

Related U.S. Application Data

(63) Continuation of application No. 16/478,640, filed as application No. PCT/US2019/016708 on Feb. 5, 2019, now Pat. No. 11,547,768.

(60) Provisional application No. 62/626,483, filed on Feb. 5, 2018.

(51) Int. Cl.
| | |
|---|---|
| *A61L 2/10* | (2006.01) |
| *A47L 7/00* | (2006.01) |
| *A47L 9/10* | (2006.01) |
| *A47L 9/24* | (2006.01) |

(52) U.S. Cl.
CPC .................. *A61L 2/10* (2013.01); *A47L 7/00* (2013.01); *A47L 7/0061* (2013.01); *A47L 9/10* (2013.01); *A47L 9/24* (2013.01); *A61L 2202/11* (2013.01); *A61L 2202/14* (2013.01); *A61L 2202/16* (2013.01); *A61L 2202/17* (2013.01)

(58) Field of Classification Search
None
See application file for complete search history.

(56) References Cited

U.S. PATENT DOCUMENTS

| | | |
|---|---|---|
| 5,343,629 A | 9/1994 | Rae |
| 7,444,711 B2 | 11/2008 | Garcia |
| 8,779,391 B2 | 7/2014 | Flaherty |
| 2005/0022844 A1 | 3/2005 | Field |

(Continued)

FOREIGN PATENT DOCUMENTS

| | | | | |
|---|---|---|---|---|
| DE | 112008001234 T5 | * | 3/2010 | ............... A47L 5/14 |
| JP | 2008-132156 A | | 6/2008 | |
| KR | 101724447 B1 | | 4/2017 | |

*Primary Examiner* — Andrew Smyth
(74) *Attorney, Agent, or Firm* — Kevin J Fournier Intellectual Property Legal Services Ltd.; Kevin J Fournier

(57) ABSTRACT

Embodiments of a unified airflow system for ultraviolet disinfection devices are disclosed. One embodiment of the present disclosure includes a unified airflow assembly and a control unit. The unified airflow assembly provides a shared airflow passage between a UV source and an airflow accessory capable of extracting contaminants from a target surface using a suction airstream. The UV source may be fluidically disconnected from the airflow accessory. The unified airflow assembly may include at least one air restriction unit in the shared airflow passage for manipulating a suction airstream therein. The control unit may be configured to drive the at least one air restriction unit to restrict the suction airstream to only one of the UV source and the airflow accessory.

20 Claims, 36 Drawing Sheets

(56) References Cited

U.S. PATENT DOCUMENTS

| | | | |
|---|---|---|---|
| 2005/0154075 A1* | 7/2005 | Siegel | C09D 11/101 |
| | | | 522/8 |
| 2006/0185115 A1* | 8/2006 | Yoo | A47L 5/32 |
| | | | 15/334 |
| 2008/0056933 A1 | 3/2008 | Moore | |
| 2010/0313379 A1* | 12/2010 | Milanese | A47L 9/0411 |
| | | | 15/339 |
| 2012/0223216 A1* | 9/2012 | Flaherty | G05D 1/0242 |
| | | | 901/1 |
| 2012/0246863 A1* | 10/2012 | Douglas | A47L 7/0061 |
| | | | 29/428 |
| 2016/0296649 A1* | 10/2016 | Ramanand | A61L 2/10 |

* cited by examiner

UNIFIED AIRFLOW SYSTEM FOR ULTRAVIOLET DISINFECTION DEVICES

PRIORITY CLAIM AND CROSS REFERENCE TO RELATED APPLICATIONS

The present patent application is a continuation of U.S. Non-Provisional patent application Ser. No. 16/478,640, filed Jul. 17, 2019, which is a U.S. National Stage Application of PCT International Application No. PCT/US2019/016708, filed Feb. 5, 2019, and published on Aug. 8, 2019 as PCT International Application Publication No. WO 2019/153014, which claims priority to U.S. Provisional Patent Application Ser. No. 62/626,483, filed Feb. 5, 2018, all of which are incorporated herein by reference in their entireties. The present patent application incorporates the subject matter of the following patent applications, by reference and in their entirety: U.S. Non-Provisional patent application Ser. No. 15/095,212, filed Apr. 11, 2016, and titled "TARGETED SURFACE DISINFECTION DEVICE WITH PULSED UV LIGHT" and U.S. Provisional Patent Application Ser. No. 62/626,483, filed Feb. 5, 2018, and titled "AN ULTRAVIOLET DISINFECTION DEVICE WITH A CLEANING UNIT," in which the inventors herein were listed as co-inventors.

TECHNICAL FIELD

The subject matter described herein generally relates to ultraviolet (UV) disinfection devices and particularly relates to a unified airflow system for UV disinfection devices.

BACKGROUND

Ultraviolet (UV) light is widely known for contactless surface disinfection. When used in addition to contact-based surface cleaning tasks, brushing, wiping, etc., UV-based disinfection enhances pathogen deactivation on surfaces such as door knobs, cupboards, and floors. Of late, various surface cleaning equipment have become available with UV disinfection capabilities. One such surface cleaning equipment is a floor vacuum-cleaner fitted with a UV lamp that emits UV light to deactivate pathogens White extracting dirt from a floor. However, the extent of such UV disinfection is limited by the positioning of UV lamp on the vacuum cleaner.

In one approach, the UV lamp is typically positioned proximate to a suction opening or an air-nozzle of the vacuum cleaner. Since the air drawn into the air-nozzle via the suction opening becomes unclean with dirt, the UV lamp is typically screened to prevent any operational interference by the unclean air. However, such screening prevents the drawn an from cooling-off the UV lamp that heats-up during operation, thereby deteriorating life and performance of the UV lamp over time. Moreover, the UV lamp, at such positions, projects the UV light towards the floor or adjacent lower surfaces such as floor baseboards, and is unable to disinfect surfaces, e.g., table tops, door knobs, etc., located at a substantial height from the floor. As a result, the UV disinfection is limited to surfaces close to the ground or those of the vacuum cleaner itself such as the vacuum cleaner body.

In another approach, the UV lamp is usually located away from the suction opening or the air nozzle, for example, on top of the vacuum cleaner body. Although the UV lamp thus projects the UV light away from the floor, an additional component such as a fan is typically required to cool-off the UV lamp installed at these locations. Such additional component amplifies the manufacturing or assembly cost and increases an Overall weight of the vacuum cleaner to impede easy maneuverability. Moreover, at a set orientation, the UV lamp projects the UV light to a narrow surface area causing significant delays when attempting to disinfect a large area such as a room.

On the other hand, traditional area or room UV disinfection devices are used along with the conventional surface cleaning equipment such as mops and floor vacuum cleaners for faster and cc/holistic decontamination. However, such use of additional cleaning equipment increases the storage and upkeep cost to make the task of everyday surface decontamination expensive and cumbersome. Moreover, typical room UV disinfection devices generate copious amounts of harmful ozone during operation that can adversely affect the health of a user over time.

SUMMARY

Embodiments of the present disclosure describe a unified airflow system for ultraviolet disinfection devices. One embodiment of the present disclosure includes a unified airflow assembly and a control unit. The unified airflow assembly provides a shared airflow passage between a UV source and an airflow accessory capable of extracting contaminants from a target surface using a suction airstream. The UV source may be fluidically disconnected from the airflow accessory. The unified airflow assembly may include at least one air restriction unit in the shared airflow passage for manipulating a suction airstream therein. The control unit may be configured to drive the at least one air restriction unit to restrict the suction airstream to only one of the UV source and the airflow accessory.

One aspect of the present disclosure is to provide an integrated device for contact and contactless decontamination.

Another aspect of the present disclosure is to provide a large-area UV disinfection device.

Yet another aspect of the present disclosure is to cool a UV lamp of the UV disinfection device that is heated-up during operation.

Still another aspect of the present disclosure is to remove contaminants from target surfaces.

Another aspect of the present disclosure is to remove harmful gases released by the UV lamp during operation.

Yet another aspect of the present disclosure is to provide a unified airflow system that is compatible with different configurations of a connected airflow accessory.

Still another aspect of the present disclosure is to provide autonomous surface decontamination through vacuum cleaning and UV disinfection.

Another aspect of the present disclosure is decontamination of surfaces, which are at a significant height from the ground.

Yet another aspect of the present disclosure is to provide effective surface disinfection through prior removal of contaminants from a surface.

Still another aspect of the present disclosure is to decontaminate and disinfect surfaces on the ground and proximate thereto.

The above summary of exemplary embodiments is not intended to describe each disclosed embodiment or every implementation of the present disclosure. Other and further aspects and features of the disclosure will be evident from reading the following detailed description of the embodiments, which are intended to illustrate, not limit, the present disclosure.

BRIEF DESCRIPTION OF THE DRAWINGS

The illustrated embodiments of the subject matter will be better understood by reference to the drawings, wherein like parts are designated by like numerals throughout. The following description is intended only by way of example, and simply illustrates certain selected embodiments of devices, systems, and processes that are consistent with the subject matter as described herein.

FIG. 1 is a cross-sectional view of the wearable airflow accessory of FIG. 9 taken along the line A-A of FIG. 9, according to an embodiment of the present disclosure.

DETAILED DESCRIPTION

Figure 1:
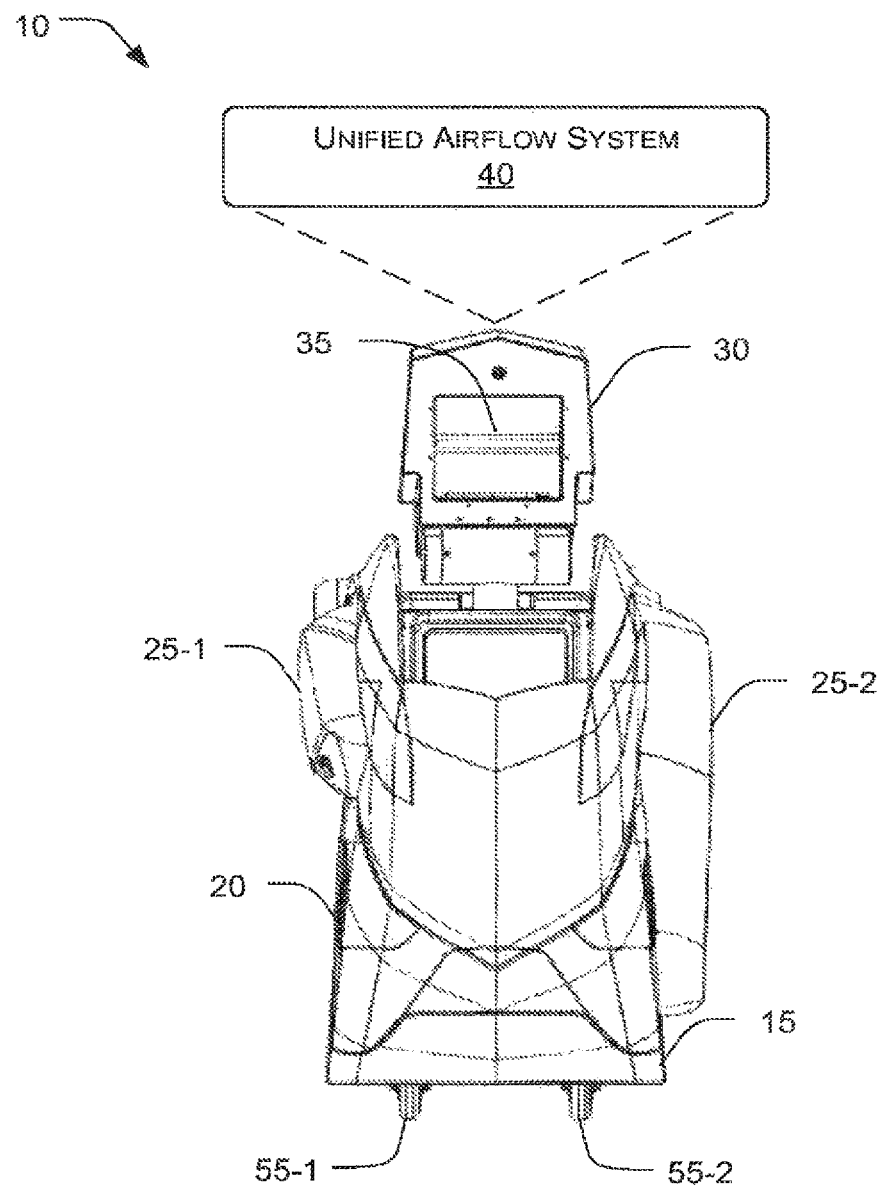
FIG. 1 is a front elevation view of an area ultraviolet (UV) disinfection device including an exemplary unified airflow system, according to an embodiment of the present disclosure illustrating a cabinet and an articulated head assembly in an open position.
Figure 2:
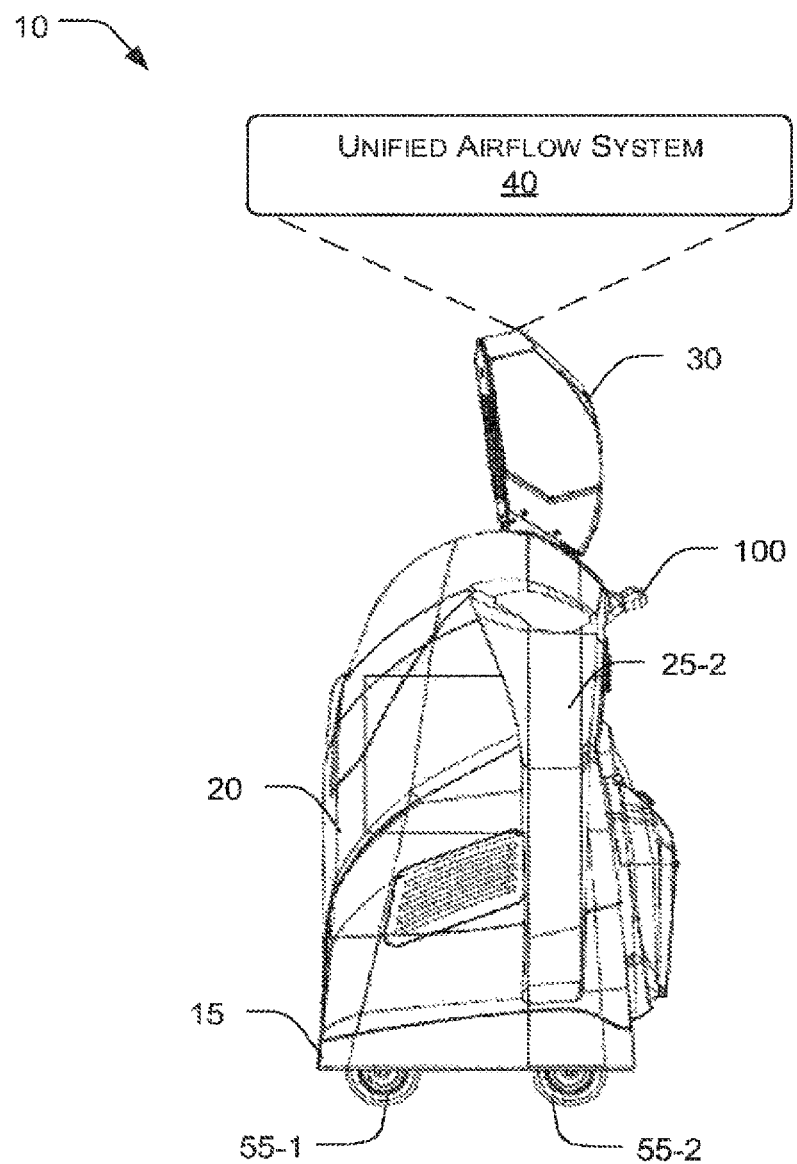
FIG. 2 is a right-side elevation view of the area UV disinfection device of FIG. 1, according to an embodiment of the present disclosure.
Figure 3:
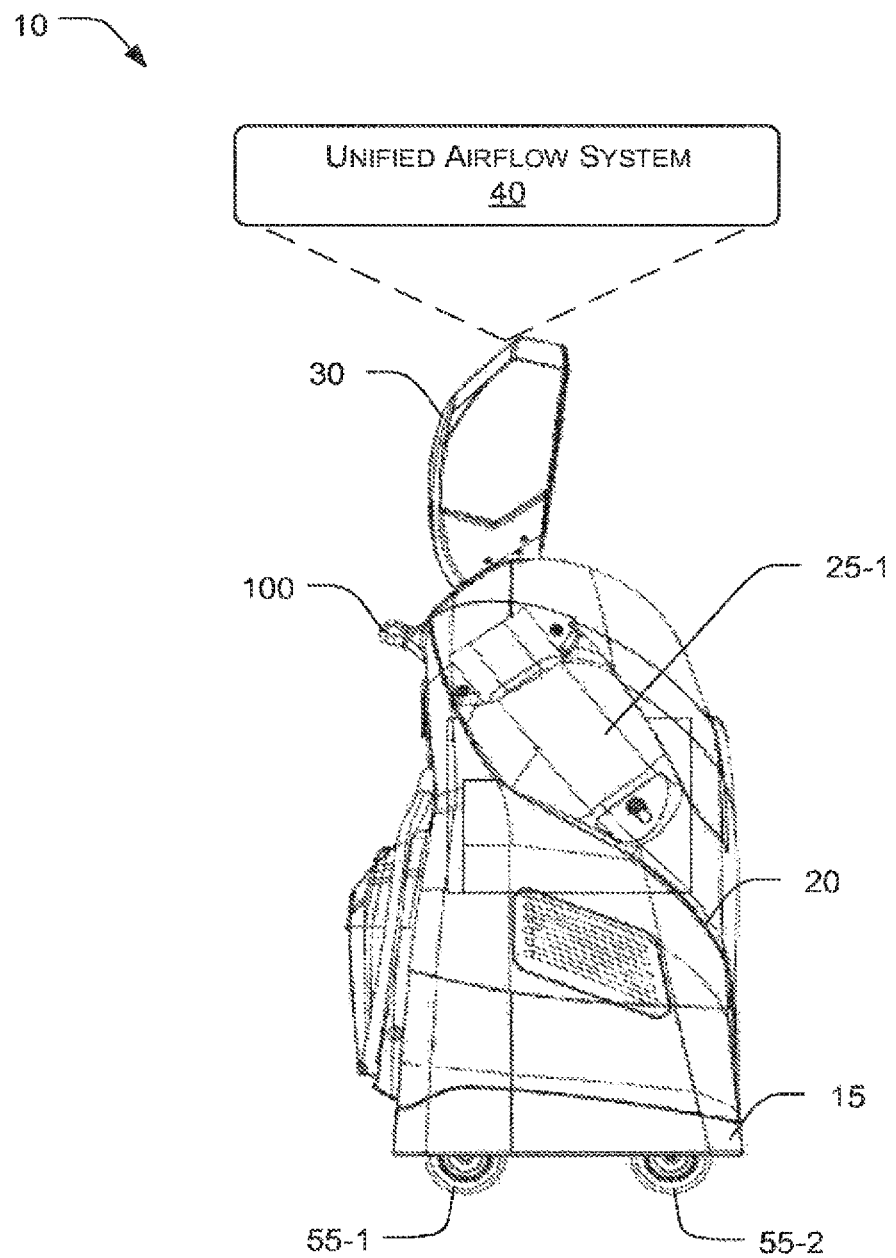
FIG. 3 is a left-side elevation view of the area UV disinfection device of FIG. 1, according to an embodiment of the present disclosure.
Figure 4:
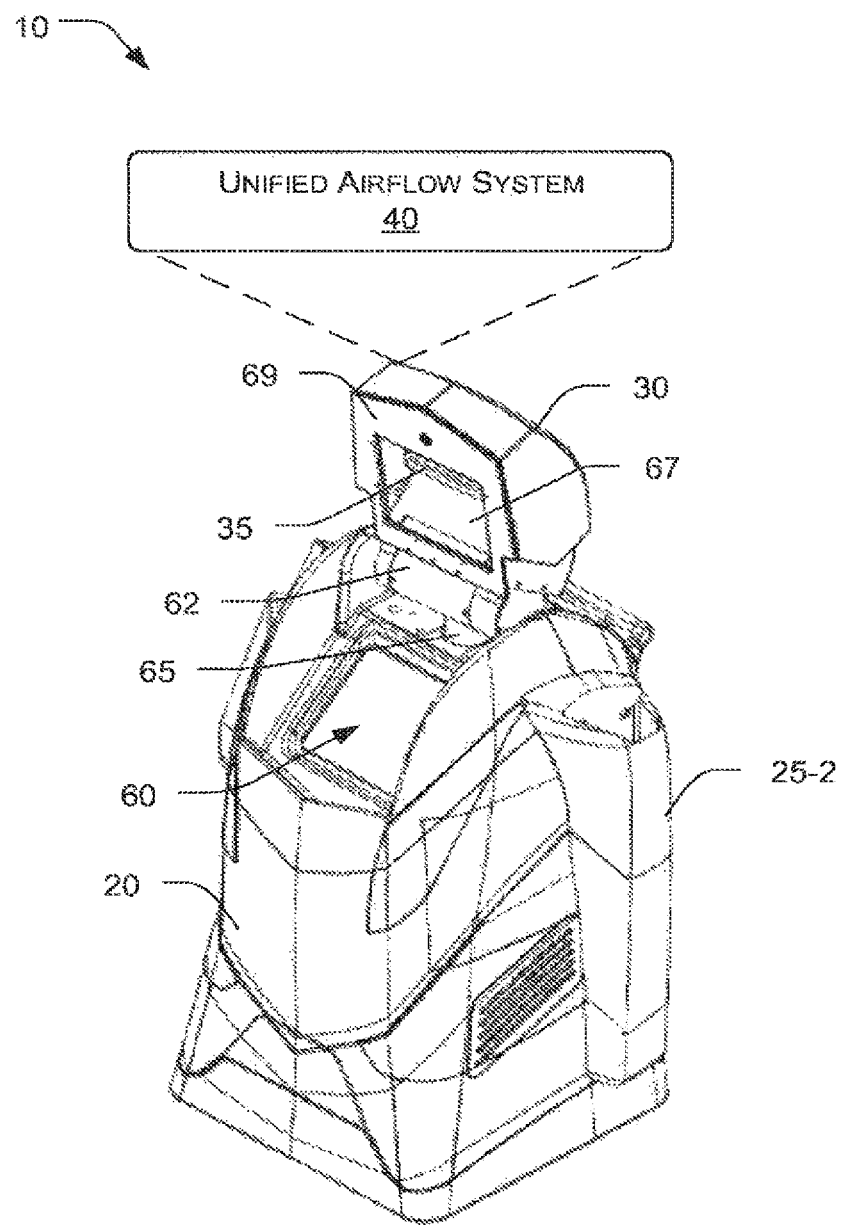
FIG. 4 is a front isometric view of the area UV disinfection device of FIG. 1 illustrating the right-side of the area UV disinfection device, according to an embodiment of the present disclosure.
Figure 5:
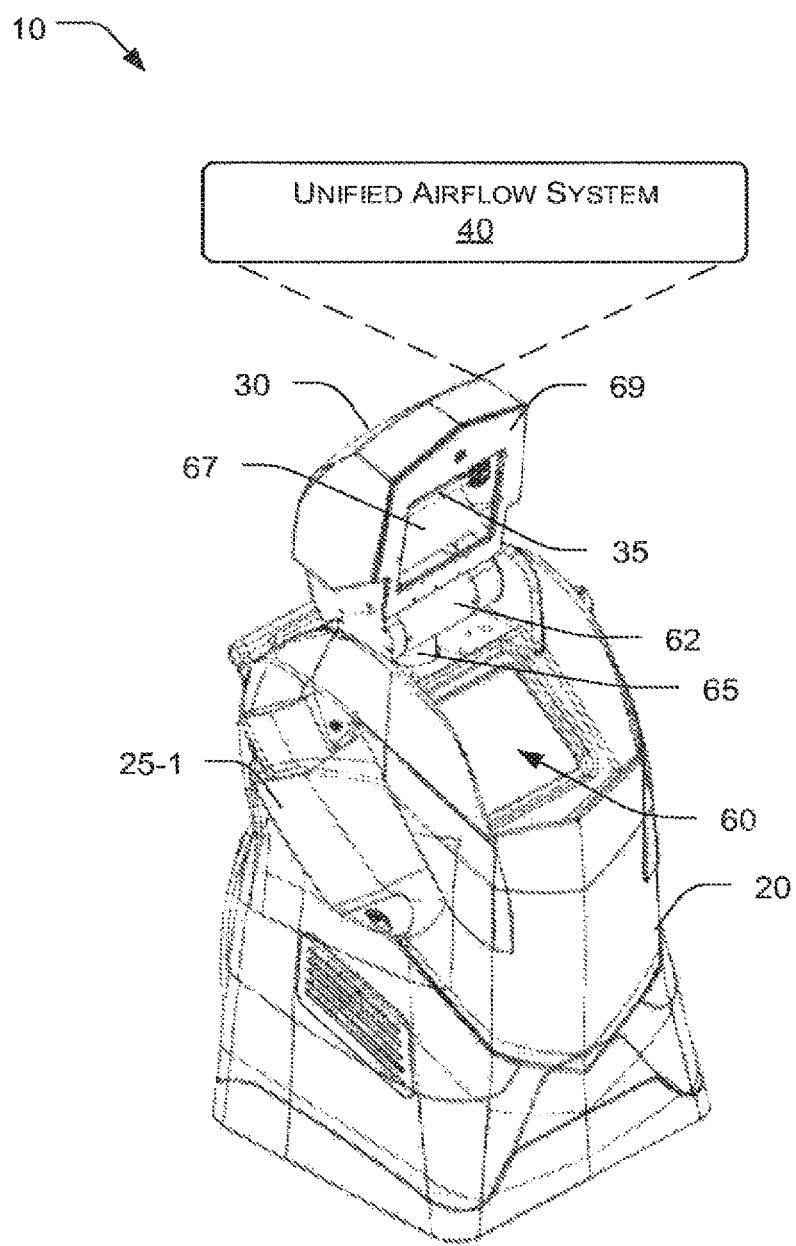
FIG. 5 is a front isometric view of the area UV disinfection device of FIG. 1 illustrating the left-side of the area UV disinfection device, according to an embodiment of the present disclosure.

The following detailed description is provided with reference to the figures. Exemplary embodiments are described to illustrate the disclosure, not to limit its scope, which is defined by the claims. Those of ordinary skill in the art will recognize number of equivalent variations in the description that follows without departing from the scope and spirit of the disclosure.

Non-Limiting Definitions

Definitions of one or more terms that will be used in this disclosure are described below without limitations. For a person skilled in the art, it is understood that the definitions are provided just for the sake of clarity and are intended to include more examples than just provided below.

A "ultraviolet disinfection device" is used in the present disclosure in the context of its broadest definition. The ultraviolet (UV) disinfection device may refer to a standalone or a networked electronic or electromechanical device capable of providing pulses of ultraviolet (UV) radiation of a desired intensity, dose or frequency within the germicidal wavelength range of the UV spectrum for disinfection.

"Decontamination" is used in the present disclosure in the context of its broadest definition. The decontamination may refer to removal or neutralization of unwanted substances from a target surface or enveloping atmosphere.

"Disinfection" is used in the present disclosure in the context of its broadest definition. The disinfection may refer to any process of inactivating or killing pathogens on a target surface using UV light alone or in combination with a variety of disinfectants known in the art, related art, or developed later including, but not limited to, chemical agents (e.g., alcohols, aldehydes, oxidizing agents, naturally occurring or modified compounds, etc.), physical agents (e.g., heat, pressure, vibration, sound, radiation, plasma, electricity, etc.), and biological agents (e.g., living organisms, plants or plant products, organic residues, etc.).

A "cleaning unit" is used in the present disclosure in the context of its broadest definition. The cleaning unit may refer to a networked, interconnected or a standalone device capable of using fluid, pressure either alone or in combination with one or more cleaning agents to decontaminate a surface. Examples of cleaning agents may include, but not limited to, chemical agents, physical agents, and biological agents such as those mentioned above.

A term "proximal" is used in the present disclosure in the context of its broadest definition. The term "proximal" may refer to a side, end, portion, section, location, direction, position, or any other aspect being relatively farthest from a UV lamp in communication with the UV disinfection device.

A term "distal" is used in the present disclosure in the context of its broadest definition. The term "distal" may refer to a side end, portion, section, location, direction, position, or any other aspect being relatively closest to the UV lamp in communication with the UV disinfection device.

A term "airflow accessory" is used in the present disclosure in the context of its broadest definition. The airflow accessory may represent any powered or non-powered device capable of managing or manipulating flowrate, direction, physical properties (e.g., temperature, pressure, weight or mass, volume, velocity, concentration, electric charge, viscosity, etc.) or chemical properties (e.g., enthalpy, toxicity, pH value, reactivity, flammability, etc.) of a fluid, or any of its constituents, such as air for an intended purpose.

Overview

Embodiments of the present disclosure describe a UV disinfection device including a unified airflow system that supports an airflow accessory such as a cleaning unit of any configuration and cook a UV light source, such as a UV lamp emitting the UV light for disinfection. The unified airflow system includes a control unit and a unified airflow assembly having an airflow regulator and a vacuum pump. The airflow regulator may be coupled to a vacuum pump creating a suction airstream. The airflow regulator provides a shared air passage between the UV lamp and the airflow accessory configured to use the suction airstream for decontaminating a surface, where the UV lamp and the airflow accessory are fluidically disconnected from each other. The airflow regulator includes at least one air restriction unit being controlled by the control unit to selectively establish a fluid communication between the vacuum pump and either the UV lamp or the airflow accessory using one or more hoses. The air restriction unit facilitates the hot air around the UV light source being drawn using the suction airstream while preventing an unclean air from the airflow accessory front moving across to the UV lamp, and vice versa.

Exemplary Embodiments

The present disclosure is described below in detail with reference to the drawings, which are provided as illustrative examples so as to enable those skilled in the art to practice the disclosure. Moreover, where certain elements of the present disclosure can be partially or fully implemented using known components, only those portions of such known components that are necessary for an understanding of the present invention will be described, and detailed descriptions of other portions of such known components will be omitted. In the present specification, an embodiment showing a singular component should not be considered limiting; rather, it is intended to encompass other embodiments including a plurality of the same component, and vice-versa, unless explicitly stated otherwise herein.

FIGS. 1-5 illustrate an area ultraviolet disinfection device including an exemplary unified airflow system, according to an embodiment, of the present disclosure. Embodiments are disclosed in the context of contact and contactless surface decontamination of a large area such as a hospital room. However, in general, such and further embodiments of the present disclosure may be applied in other environments including, but not limited to, clinics, food processing facilities, cruise ships, homes, schools, factories, restaurants, ambulances, locker rooms, and gyms.

The area UV disinfection device 10 (or UVD device 10) may represent a wide variety of devices configured to emit or facilitate emission of UV pulses having predetermined characteristics suitable to induce an intended effect (e.g., disinfection, curing, sintering, etc.) on a surface in a short period (e.g., approximately 10 minutes or less) from a relatively long distance (e.g., greater than approximately 1 meter from the surface). Examples of these characteristics include, but are not limited to, energy, frequency, power, wavelength, and dose. The UVD device 10 may be implemented to include hardware and installed software, where is closely matched to the requirements and/or functionality of the hardware. In some instances, the UVD device 10 may enhance or increase the functionality and/or capacity of a network (not shown) to which it may be connected.

The network may include any software, hardware, or computer applications that can provide a medium to exchange signals or data in any of the formats known in the art, related art, or developed later. The network may include, but is not limited to, social media platforms implemented as a website, a unified communication application, or a stand-alone application. Examples of the social media platforms may include, but are not limited to, Twitter™. Facebook™, Skype™, Microsoft Lync™. Cisco Webex™, and Google Hangouts™. Further, the network may include, for example, one or more of the Internet, Wide Area Networks (WANs), Local Area Networks (LANs), analog or digital wired and wireless telephone Networks (e.g., a PSTN, Integrated Services Digital Network (ISDN), a cellular network, and Digital Subscriber Line (xDSL), radio, television, cable, satellite, and/or any other delivery or tunneling mechanism for carrying data. The network may include multiple networks or sub-networks, each of which may include, e.g., a wired or wireless data pathway. The network may include a circuit-switched voice network, a packet-switched data network, or any other network able to carry electronic communications. For example, the network may include networks based on the Internet protocol (IP) or asynchronous transfer mode (ATM), and may support voice using, for example, VoIP, Voice-over-ATM, or other comparable protocols used for voice, video, and data communications.

The UVD device 10 may also include software, firmware, or other resources that support remote administration, operation, diagnostics, repair, and/or maintenance thereof. Further, the UVD device 10 may be implemented in communication with any of a variety of computing devices such as a desktop PC, a personal digital assistant (PDA), a server, a mainframe computer, a mobile computing device (e.g., mobile phones, laptops, etc.), an internet appliance (e.g., a DSL modem, a wireless access point, a router, a base station, a gateway, etc.), and so on. In some instances, the UVD device 10 may operate, or cease to operate, in response to a wearable device including, but not limited to, a fashion accessory (e.g., a wristband, a ring, etc.), a utility device (hand-held baton, a pen, an umbrella, a watch, etc.), a body clothing, or any combination thereof, present within a predetermined proximity of, or remotely connected to, the UVD device 10.

The UVD device 10 either independently or in communication with a network device may have video, voice, or data communication capabilities (e.g., unified communication capabilities) by being coupled to or including, various imaging devices (e.g., cameras, printers, scanners, medical imaging systems, etc.), various audio devices (e.g., microphones, music players, recorders, audio input devices, speakers, audio output devices, telephones, speaker telephones, etc.), various video devices (e.g., monitors, projectors, displays, televisions, video output devices, video input devices, camcorders, etc.), or any other type of hardware, in any combination thereof. In some instances, the UVD device 10 may comprise or implement one or more real-time protocols and non-real-time protocols known in the art, related art, or developed later to facilitate data transfer to the networked device.

In one embodiment, the UVD device 10 may include a mobile carriage 15, a cabinet 20, a first utility pod 25-1, a second utility pod 25-2, a head assembly 30, a UV lamp 35, a unified airflow system 40, a display unit 45, and an, airflow accessory 50. The mobile carriage 15 may provide a platform for supporting various components such as the cabinet 20 and the UV lamp 35 of the UVD device 10. The mobile carriage 15 may include mobility devices, which may assist to drive the mobile carriage 15 on an intended surface such as a floor based on friction, magnetic levitation, cryogenic levitation, or any other motion principle known in the art, related art, or developed later. For example, the mobile carriage 15 may include omnidirectional wheels 55-1 and 55-2 for navigating the UVD device 10 with precision to any desired location within a designated space such as a hospital room. The mobile carriage 15 may be controlled remotely by any computing device known in the art, related art, or developed later such as those mentioned above over the network. In some instances, the mobile carriage 15 may be configured to operate or move autonomously. For example, the mobile carriage 15 may be fitted with electric motors connected to the mobility devices, where the electric motors may be controlled remotely via a control box such as a control unit 150, discussed in detail below. The mobile carriage 15 may be partially or fully enclosed in the cabinet 20.

The cabinet 20 may refer to any housing configured to substantially cover the mobile carriage 15 and protect various components mounted thereon. In some instances, the cabinet 20 may improve the aesthetics of the UVD device 10. The cabinet 20 may be made of any durable, fire-retardant or fire-resistant, and light-weight polymers known in the art, related art, or developed later including, but not limited to, polyphenylene sulfide, polyamide-imide, polypropylene, and aramid polyamide polymers. The cabinet 20 may include components or pockets that may be permanently connected, detachably coupled, or integrally formed thereto, based on intended purposes. For example (FIGS. 2-3), the cabinet 20 may include a handle 100 for enabling a user to manually maneuver the UVD device 10 from one place to another. In another example, one or more utility pods such as the first utility pod 25-1 and the second utility pod 25-2 (collectively, pods 25) may be attached externally to the cabinet 20, allowing for convenient on-board carrying of various tools, supplies and implements, such as wands, mop head/handles, boxes of wet-wipes or mop-refills, etc. Structurally, such pods 25 may be hollow tridimensional structures, with at least one staple opening and rigid or semi-rigid walls. In some instances, such staple opening may face generally upwards or at a predetermined angle for easy access.

The pods 25 may have any of a variety of shapes such as a rectangular prismatic (or oval prismatic) shape, which may be either attached to the cabinet 20 at various suitable positions or may be pre-molded (or preformed) onto the cabinet 20 at the cabinet manufacturing stage, Functionally, such pods 25 may serve to hold (or stow) various tools, supplies and implements, such as wands, mop heads/handles, boxes of wet-wipes or mop-refills, cleaning supplies, etc. in a proximity which gives convenience and easy reach to a human operator. These pods 25 may have different structural configurations. For example, the first utility pod 25-1 may be a shorter (less deep) and wider pod, e.g., suitable for boxes of mop heads, boxes of wet-wipes or mop-refills, cleaning supplies, short wands, short-handled cleaning implements, handheld vacuum cleaners, etc. By contrast, the second utility pod 25-2 may be a relatively longer (deeper) pod, suitable for stowing longer and/or narrower implements, such as long wands and long mop-handles. Other structural configurations may include the pods 25 having any suitable dimensions, structures, or shapes depending on items intended to be carried or engaged therewith. Such pods 25 may be placed in any suitable position, e.g., outside (or extending towards inside) the cabinet 20, provided such placement does not interfere with the intended functionality of the UVD device 10.

Various other kinds, sizes, and shapes of utility pods 25 may also be contemplated based an intended purpose or items to be held therein, such as refuse-holding pods, pods for dirty (or used) wipes, pods for holding various tools and electrical cords, pods with optional lids and liners, pods for documents and paperwork, pods with openings both at the top and at the bottom, pods placed entirely or partially within the inside volume of cabinet 20, etc. The pods 25 may be made of any suitable material known in the art, related art, or developed later including those described above for the cabinet 20, such that the material has suitable rigidity, mechanical tolerance, and resistance to the UV light or various other types of decontamination and disinfection agents known in the art, related art, or developed later. Adjacent to the pods 25 (FIGS. 4-5), the cabinet 20 may include a recess 60 for receiving the head assembly 30, or a portion thereof, in a retracted position. However, other suitable locations may be contemplated for the recess 60 on the cabinet 20 based on functional and structural configurations of the head assembly 30.

The head assembly 30 may be supported on the mobile carriage 15 and secured to a vertical journal 65, which may be selectively rotated by a motor (not shown), thereby allowing the head assembly 30 to follow a panning motion about a vertical axis in an open position, as illustrated. The vertical journal 65 may be connected to a motorized tilt mechanism 62, which may rotate about a horizontal axis parallel to the floor for selectively pivoting the head assembly 30 from the open position to a retracted position (not shown), and vice versa. The motorized tilt mechanism 62 in combination with the vertical journal 65 may allow precise pan, swivel, tilt, and rotatory movements of the head assembly 30. In the retracted position, the head assembly 30 may be seated within the recess 60 of the cabinet 20.

In one embodiment, the head, assembly 30 may include the UV lamp 35 configured to orient in different directions for projecting the UV light depending on the movement of the head assembly 30. For example, in the illustrated open position, the head assembly 30 may move out of the recess 60 and tilt to a predetermined angle with respect to the horizontal axis for allowing the UV lamp 35, upon activation, to project the UV light through a quartz window 67 in a front panel 69 of the head assembly 30. Such tilt of the head assembly 30 may depend on the height of a target surface from the ground. For example, the head assembly 30 may be tilted, substantially downwards about the horizontal axis for the UV lamp 35 to project the UV light through the quartz window 67 on to the ground and/or surfaces proximate thereto, e.g., zero to approximately 2 feet from the ground. In another example, the head assembly 30 may be tilted substantially upwards about the horizontal axis for the UV lamp 35 to project the UV light through the window 67 on to a ceiling and/or surfaces proximate thereto such as 8 feet to 10 feet from the ground. Other examples may include the head assembly 30 being tilted to fixed or gradually changing angles for projecting the UV light on target surfaces at a substantial height, e.g., approximately 2 feet to approximately 8 feet, from the ground.

Further, in the retracted position of the head assembly 30, the UV lamp 35 may be deactivated; however, some embodiments may include the UV lamp 35 being configured to emit the UV light to a predetermined site within the UVD device 10 in such retracted position. In some other embodiments may include movement and orientation of the UV lamp 35 being independent of the movement of the head assembly 30. Further embodiments may include additional UV sources such as the UV lamp 35 enclosed in a housing and placed at other suitable locations on the UVD device 10. Examples of these locations may include, but not limited to, outer surface of the cabinet 20 and the mobile carriage 15.

The UV lamp 35 may be of any suitable type known in the art, related art, Or developed later including a mercury-vapour UV lamp 35, a pulsed Xenon UV lamp 35, and a continuous UV lamp 35, The UV lamp 35 may be configured to irradiate timed pulses of UV light with each pulse having predefined characteristics such as energy, power, wavelength, and frequency according to an intended application such as disinfection and a distance between the UV lamp 35 and a target surface. For example, the UV lamp 35 may be controlled by the control unit 150 to emit 30 to 1500 Joules of energy per pulse of UV light at a predefined frequency ranging from 2-100 Hz for a distance of approximately 1 to approximately 3 meters between the UV lamp 35 and a target surface. Other suitable pulse characteristics may be contemplated for effective disinfection at greater distances from the target surface. Such pulse characteristics and other aspects (e.g., operational duration, temperature, ozone gas Concentration, etc.) of the UV lamp 35 may be displayed on the display unit 45, discussed below, in communication with the UVD device 10.

In one embodiment, the head assembly 30 may be in flow communication with the unified airflow system 40 configured for manipulating a fluid pressure to assist decontamination of regions internal as well as external to the UVD device 10. The unified airflow system 40 may establish a selective flow communication between sites inside and outside the UVD device 10. The unified airflow system 40 may be further configured to (1) provide a common or shared fluid passage between a predetermined site and various other sites, which may be fluidically disconnected from each other, and (2) manipulate the pressure or direction of a circulating fluid such as air between the predetermined site and those other sites.

Figure 6:
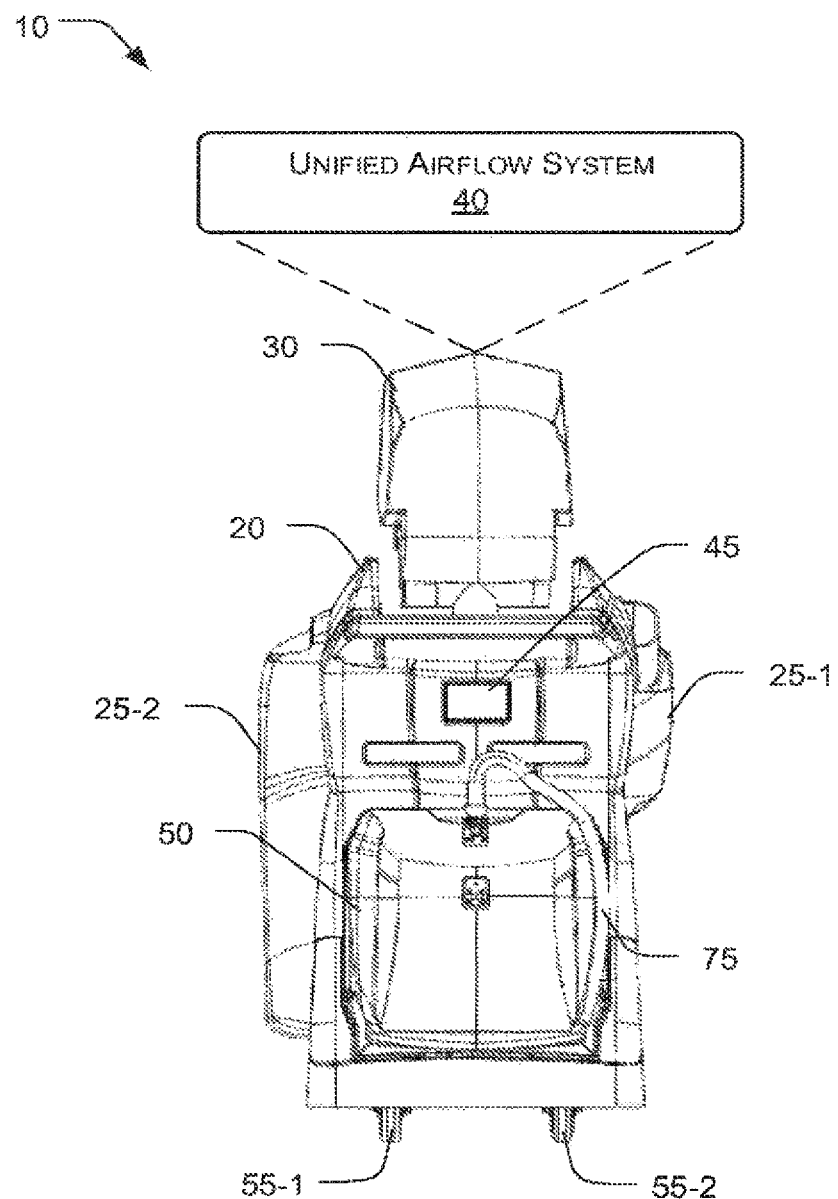
FIG. 6 is a rear elevation view of the area UV disinfection device including an exemplary fixed airflow accessory for being used with the unified airflow system of FIG. 1, according to an embodiment of the present disclosure.
Figure 7:
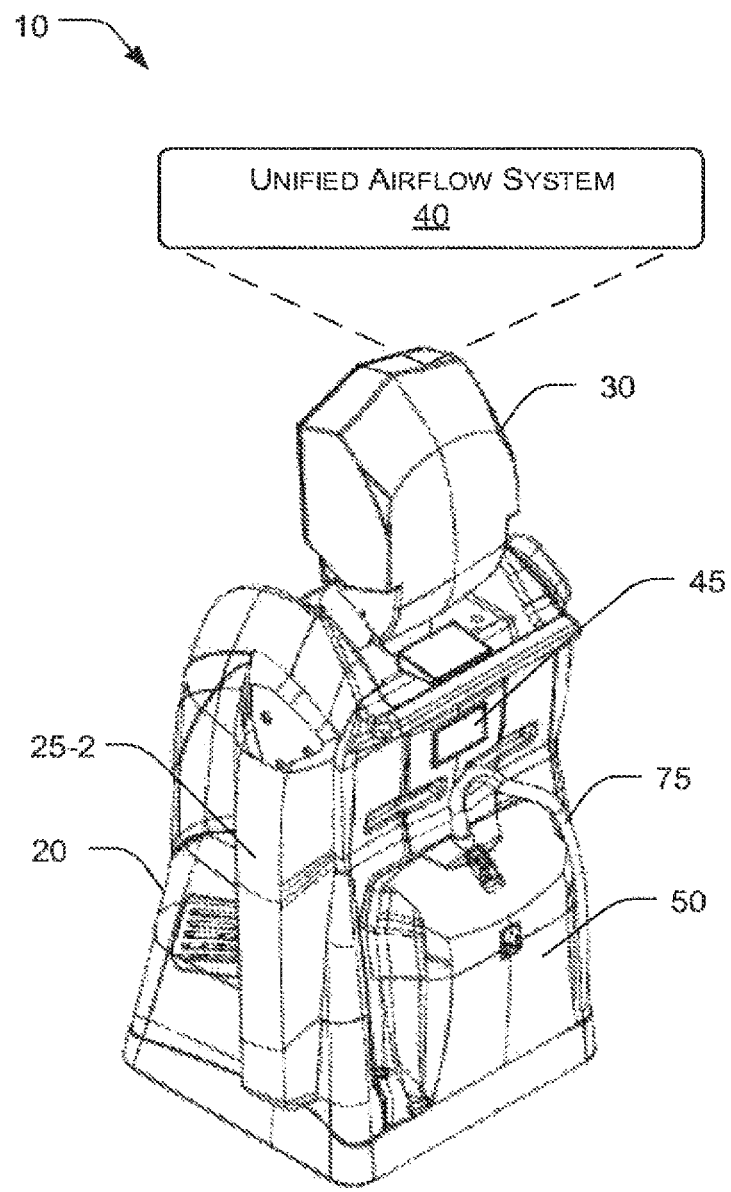
FIG. 7 is a rear isometric view of the area UV disinfection device of FIG. 6 illustrating, the right-side of the area UV disinfection device, according to an embodiment of the present disclosure.

Further, in the illustrated embodiment (FIGS. 6-7), the UVD device 10 may further include the display unit 45 located on the cabinet 20; however, other embodiments may include the display unit 45 connected remotely to the UVD device 10 over the network. The display unit 45 may be in communication with a user interface. (not shown) indicating information pertaining to the operation of UVD device 10. Different types of user interfaces, including those, which are touch controlled, key-controlled, joystick-controlled, motion-controlled, voice-controlled, and so on may be employed. The user interface may be either integrated or separately combined with the display unit 45 or the device 10, which may also include a variety of known, related art, or later developed interface(s), including software interfaces (e.g., an application programming interface, a graphical user interface, etc.); hardware interfaces (e.g., cable connectors, a keyboard, a card reader, a barcode reader, a biometric scanner, an interactive display screen, a printer, temperature sensors, light sensors, disinfection sensor, etc.); or both. Such interface(s) may facilitate communication between various devices such as the head assembly 30, the unified airflow system 40, the airflow accessory 50, or any other component or device associated with the UVD device 10. In, some embodiments, the interface(s) may facilitate communication with other networked devices capable of interacting with the UVD device 10 over the network.

In one embodiment, the display unit 45 may be or include an interactive display screen allowing an operator to access, control, or dynamically define different functionalities (e.g., automatic spatial movement of the UVD device 10, dynamic pathogen detection or identification, etc.) of the UVD device 10. In one example, the display unit 45 may display a login/logout section and a dashboard. The login/logout section may allow an operator to selectively gain access for using the UVD device 10. Upon being logged-in, the display unit 45 may display the dashboard providing a list of functionalities, modes, parameters, avatars, etc. that the operator may select or modify for a desired operation of the UVD device 10. Other embodiments may include the display unit 45 including or providing a variety of tangible indicators (e.g., light emitting diodes, vibrators, speakers, etc.) or virtual indicators displayable on the dashboard (e.g., numeric indicators, alphanumeric indicators, or non-alphanumeric indicators, such as different colors, different color luminance, different patterns, different textures, different graphical objects, etc.) known in the art, related art, or developed later to indicate different aspects of the UVD device 10. Examples of these aspects may include, but not limited to, values of operational parameters such as frequency, wavelength, dose, power, and energy; a selected mode in operation; operational states of different components; and operation or performance aspects of a networked or physically connected accessory.

In one embodiment, the UVD device 10 may include the airflow accessory 50 configured to operate in communication with the unified airflow system 40. The airflow accessory 50 may represent any powered Or non-powered fluid management device capable of managing or manipulating flowrate, direction, physical properties (e.g., temperature, pressure, weight or mass, volume, velocity, concentration, electric charge, viscosity, etc.) or chemical properties (e.g., enthalpy, toxicity, pH value, reactivity, flammability, etc.) of a fluid such as air, or any of its constituents, for an intended purpose. The airflow accessory 50 may be connected fluidically to the unified airflow system 40 depending on its structural or functional configuration.

Figure 8:
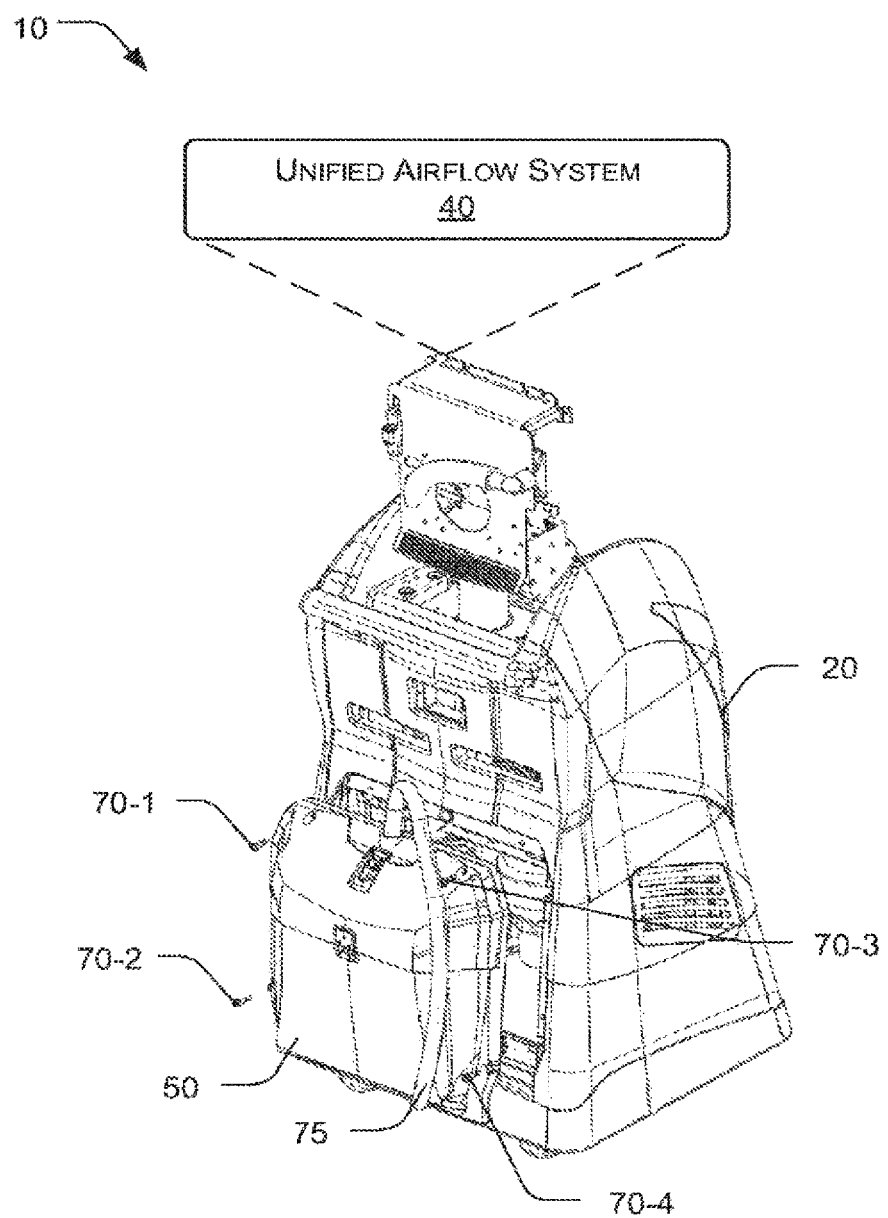
FIG. 8 is a rear isometric view of the area UV disinfection device of FIG. 1 illustrating the left-side of the area UV disinfection device with a dismounted fixed airflow accessory of FIG. 6, a portion of the cabinet removed from the head assembly, and without the utility pods, according to am embodiment of the present disclosure.
Figure 9:
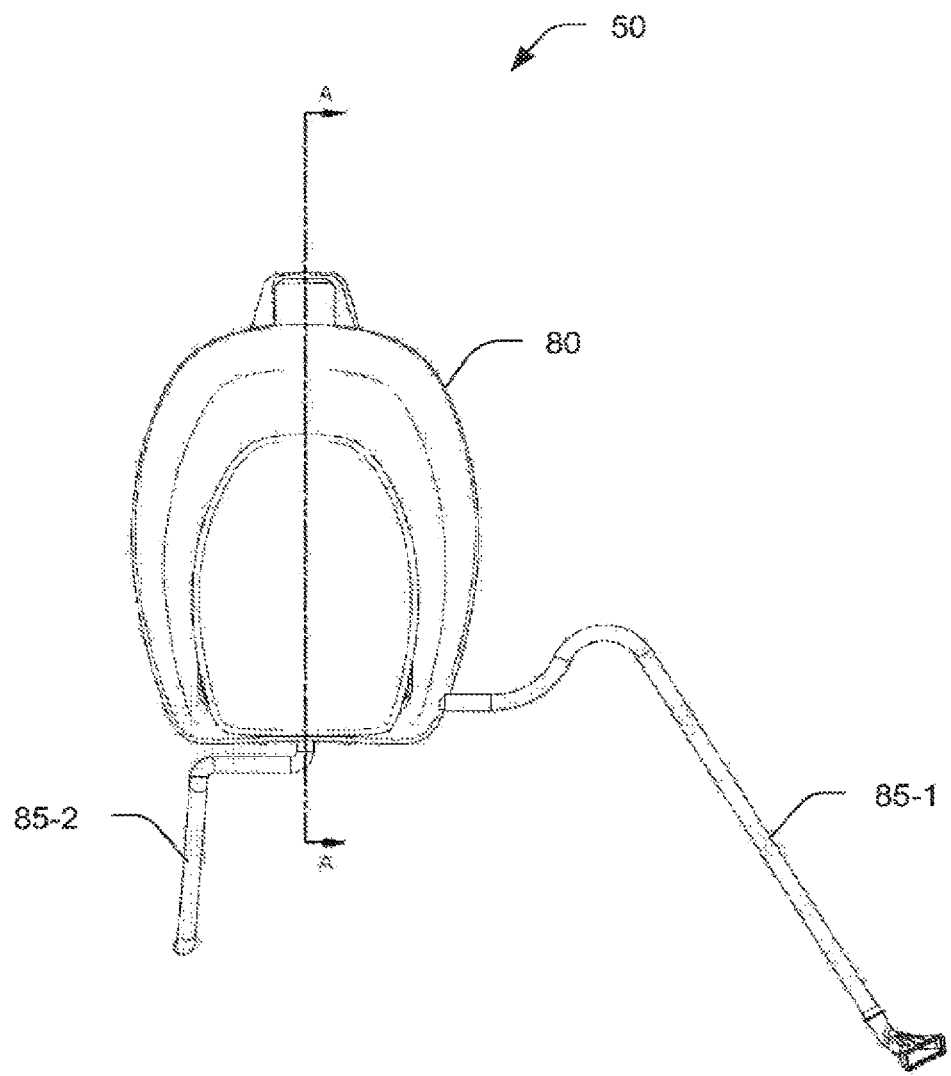
FIG. 9 is a front elevation view of an exemplary wearable airflow accessory for the unified airflow system of FIG. 1, according to an embodiment of the present disclosure.

The airflow accessory 50 may be adapted to have a variety of configurations. In a first configuration (FIGS. 6-8), the airflow accessory 50 may be configured as a fixed unit (hereinafter interchangeably referred to as fixed accessory) for being permanently connected to the cabinet 20 by screws 70-1, 70-2, 70-3, and 70-4. However, other suitable connection mechanisms known in the art, related art, or developed later including welding and gluing may be contemplated depending on materials from which the airflow accessory 50 and the cabinet 20 are made. The fixed accessory may be mounted at any suitable location away from a projection side of the cabinet 20. The projection side may refer to any location on the cabinet 20 which can fall in the path or plane of UV light emitted by the UV lamp 35 during operation in the open position of the head assembly 30. For example, the fixed accessory may be mounted on a rear side of the cabinet 20, where the rear side may be located behind the front panel 69 of the head assembly 30. Such mounting of the fixed accessory away from the projection side may prevent a human Operator of the fixed accessory from being exposed to the UV light in the event of unintentional activation of the UV tamp 35. Alternatively, the fixed accessory or Structural aspects thereof may be formed integral to a portion of the cabinet 20. The fixed accessory may be made of any suitable rigid or semi-rigid materials known in the art, related art, or developed later. Examples of such materials may include metals, polymers, composites, alloys, or the like. In one embodiment, the fixed accessory may be configured as a cleaning accessory including a cleaning unit 110 capable of collecting and storing contaminants such as dirt and debris using the unified airflow system 40, discussed below in further details. The fixed accessory, or the cleaning unit 110 therein, may also include a fixed accessory hose 75 extending proximally out from the body of the fixed accessory. The fixed accessory hose may 75 allow an operator to guide the airflow through the fixed accessory in different directions for an intended purpose. For example, the fixed accessory hose 75, directly or with a hose extension kit, may assist to use the airflow provided by the unified airflow system 40 to decontaminate surfaces at a significant height such as approximately 2 feet or more from the ground. Examples of such surfaces may include, but not limited to, door knobs, wall décor, ceilings and hanging light fixtures therefrom, etc. Other examples may include the fixed accessory hose 75 being used to access surfaces at a height of less than approximately 2 feet from the ground for decontamination. In some embodiments, the airflow accessory may be powered or controlled by components/devices in physical or network connection with the UVD device 10.

In a second configuration (Ha 9), the airflow accessory 50 may be adapted to have any suitable shape, design, and geometry for being worn by an operator during use. For example, such wearable airflow accessory 50, hereinafter interchangeably referred to as wearable accessory, may be configured as a backpack or shoulder-type unit, whereby the operator may detach the wearable accessory from the cabinet 20 or the UVD device 10 for use. The wearable accessory may include a hollow body 80 having openings (not shown) to receive a first set of hoses including a first proximal hose 85-1 and a first distal hose 85-2. The first distal hose 85-2 may be connected to the unified airflow system 40 provide a fluid channel between the hollow body 80 and the unified airflow system 40, discussed below in further details. On the other hand, similar to the fixed accessory hose 75, the first proximal, hose 85-1, directly or with a hose extension kit, may assist the operator to interact with surfaces at a significant height from the ground for an intended purpose.

Figure 10:
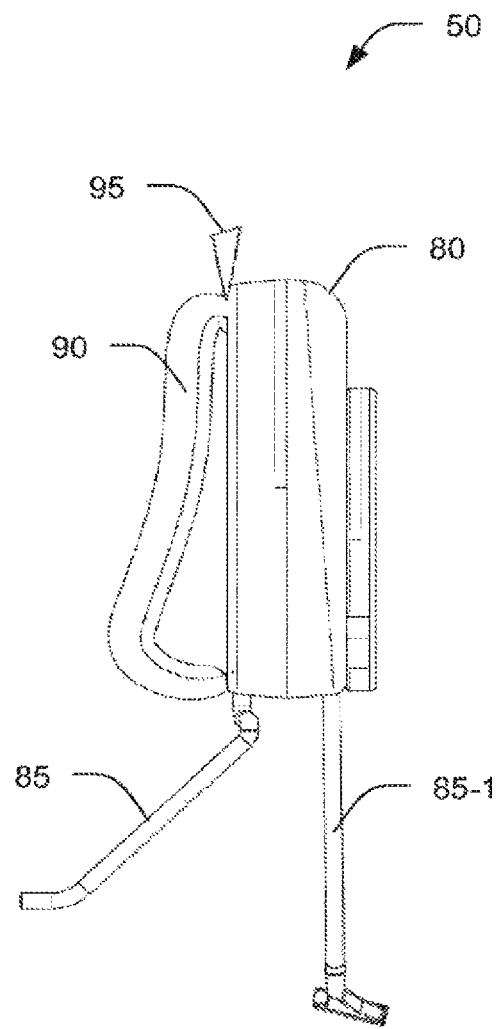
FIG. 10 is a left-side elevation view of the wearable airflow accessory of FIG. 9, according to an embodiment of the present disclosure.
Figure 11:
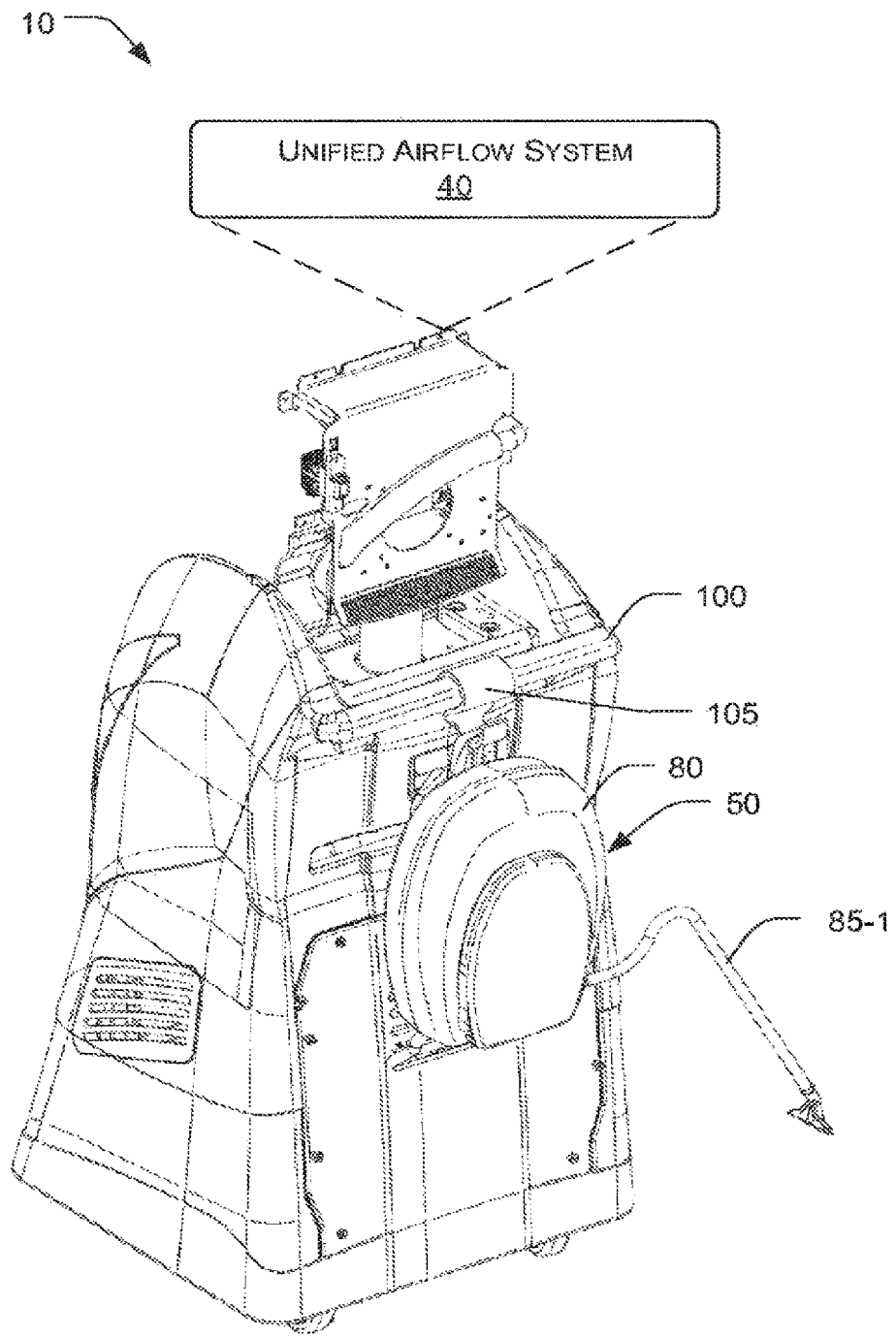
FIG. 11 is a rear isometric view of the area UV disinfection device of FIG. 1 illustrating the wearable airflow accessory of FIG. 9 being detachably mounted on the UV disinfection device and utility pods removed therefrom, according to an embodiment of the present disclosure.

The body 80 may include a pair of straps 90 and a loop 95 (FIG. 10) for easy handling or carrying the wearable accessory. The straps 90 may allow an operator to wear the wearable accessory as a normal backpack or shoulder-mounted accessory during use and thereafter, put the wearable accessory back on the UVD device 10 by any suitable accessory support 105. For, example (FIG. 11), the handle 100 of the UVD device 10 may include a hook on which the wearable accessory may be hanged by the loop 95. Other examples of such accessory support 105 may include, but are not limited to, a shelf-like structure coupled or attached to the cabinet 20 and an appropriately sized and shaped pod on the cabinet 20 in which the wearable accessory may be removably retained. The wearable accessory may be made of any suitable flexible or semi-rigid and light-weight materials known in the art, related art, or developed, later including polymers. In some embodiments, the wearable accessory may be detachably mounted on the cabinet 20 through a snap fit mechanism. Other suitable configurations known in the art, related art, or developed later including upright, cannister, robotic, and handheld configurations may also be contemplated for the airflow accessory 50.

Figure 12:
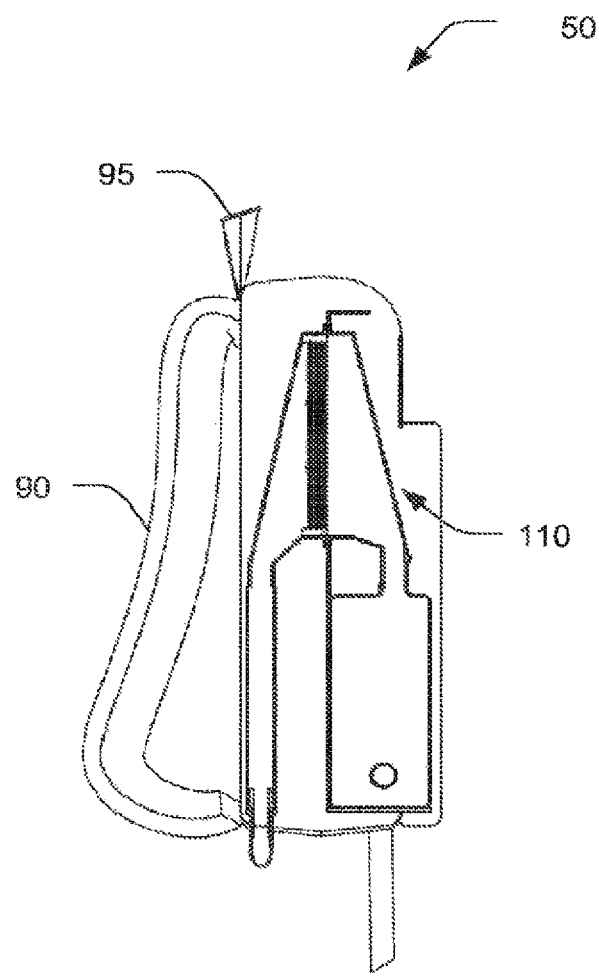
Figures 13, 14:
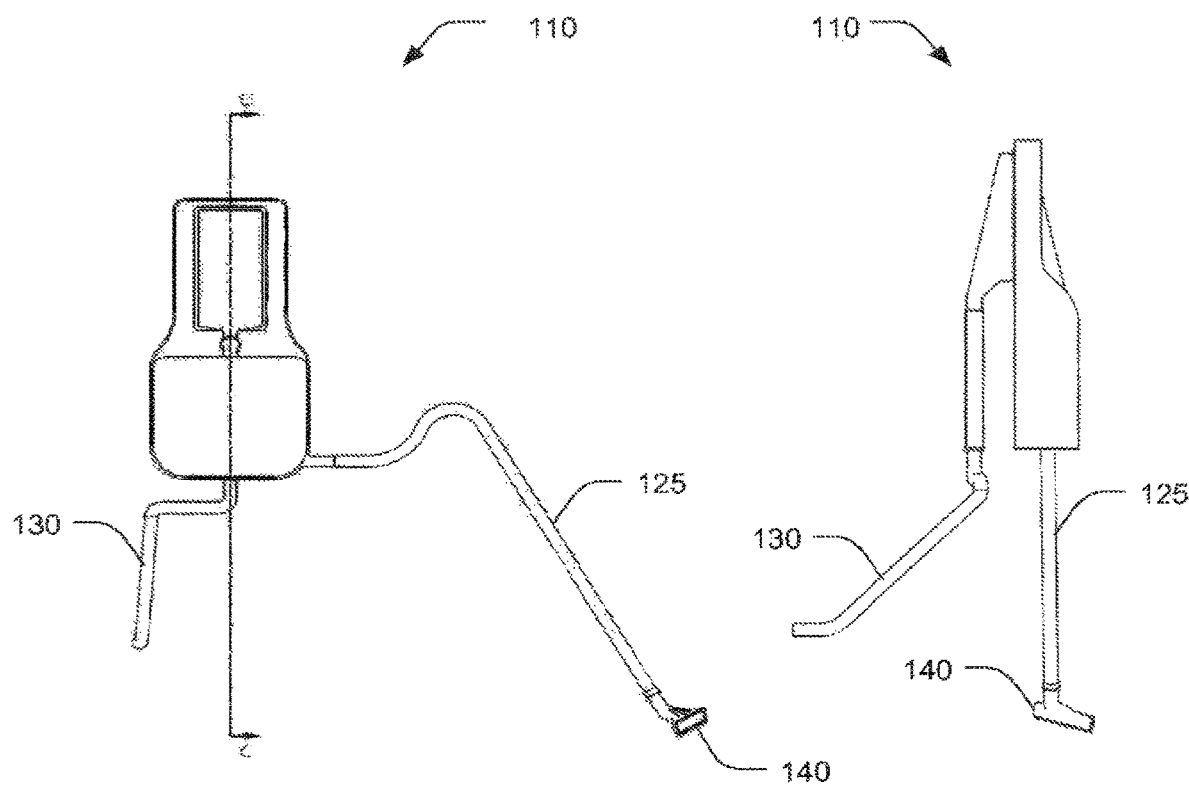
FIG. 13 is a front elevation view of an exemplary cleaning unit for the wearable airflow accessory of FIG. 9, according to an embodiment of the present disclosure.
FIG. 14 is a left-side elevation view of the cleaning unit of FIG. 13, according to an embodiment of the present disclosure.

Further, the airflow accessory 50 may be adapted for an intended purpose. For example (FIG. 12), the wearable accessory may include the cleaning unit 110 enclosed in the hollow-body 80 for surface decontamination. The cleaning unit 110 may be permanently connected, detachably installed, or formed integral to the body 80 of the wearable accessory. In one embodiment (FIGS. 13-14), the cleaning unit 110 may be a separate equipment, which may be housed within the hollow body 80 of the wearable accessory. The cleaning unit 110 may represent any of a variety of equipment capable of using a fluid such as air for contaminant collection and filtrating the contaminated fluid after such collection to produce a relatively cleaner or clearer fluid. In some embodiments, the cleaning unit 110 may be designed for being used without the airflow accessory 50 and used directly with the unified airflow system 40. The cleaning unit 110 may have any suitable shape, dimensions, or configurations depending on the desired ability to remove or collect intended contaminants such as dirt, dust, debris, and fluid waste.

Figure 15:
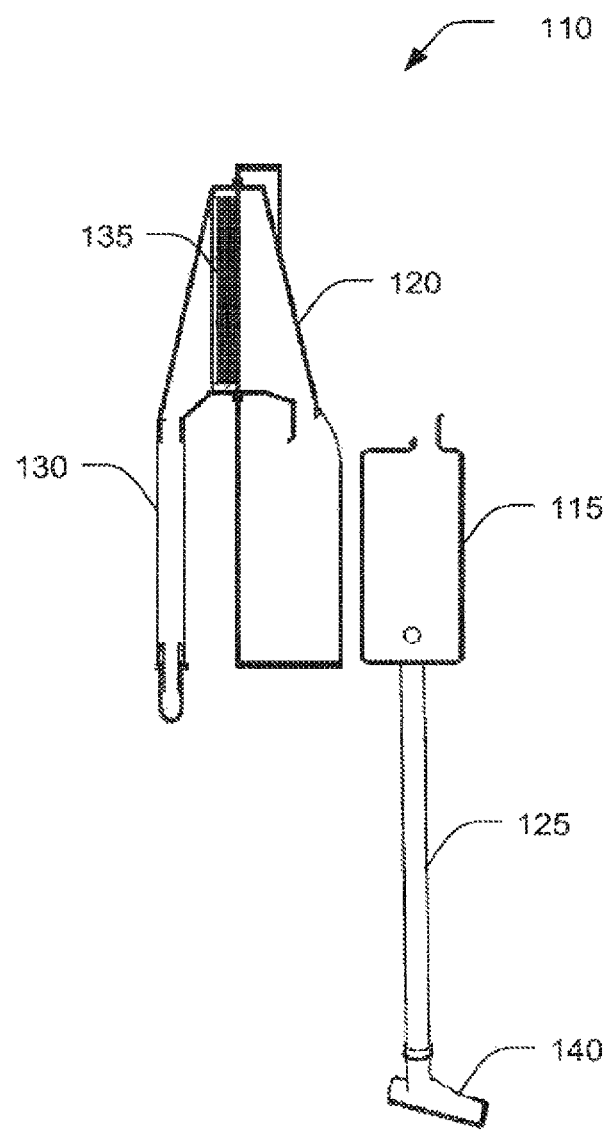
FIG. 15 is a left-side elevation view of a detached configuration of the cleaning unit of FIG. 13, according to an embodiment of the present disclosure.

In one embodiment (FIG. 15), the cleaning unit 110 may include a dirt collection unit 115 and a filtration unit 120, The dirt collection unit 115 may refer to any component or device known in the art, related art, or developed later including, but not limited to, a porous bag, a filter, or a combination thereof, capable of collecting and/or storing solid or semi-solid contaminants while allowing an intended fluid such as air, or a specific gas, to pass therethrough. Examples of materials for the porous bag may include, but are not, limited to, natural or synthetic fibers; polycomposites; foam, meshed or electrostatic paper; or any other suitable materials known in the art, related art, or developed later. The dirt collection unit 115 may be permanently connected, detachably coupled, or formed integral with a second proximal hose 125 (and/or with a hose extension kit) using any of the variety of connection mechanisms known in the art. Examples of these connection mechanisms include, but are not limited to, welding, molding, a snap fit, a screw fit, a leer-lock, and gluing, which may be chosen depending on the materials from which the dirt collection unit 115 and the second proximal hose 125 may be made. In the illustrated embodiment, the dirt collection unit 115 may be detachable from the cleaning unit 110 to assist in removing the contaminants collected therein; however, other embodiments may include the dirt collection unit 115 being integrated with the cleaning unit 110 and having a closeable opening for removing the collected contaminants.

The filtration unit 120, on the other hand, may be permanently connected, detachably coupled, or formed integral with a second distal hose 130 (and/or with a hose extension kit) using any of the variety of connection mechanisms such as those mentioned above depending on the materials from which the filtration unit 120 and the second distal hose 130 may be made. The filtration unit 120 may include an accessory filter 135, or a combination of different filters, such as those mentioned above for filtering the fluid such as air passing through the dirt collection unit 115. In the illustrated embodiment, the accessory filter 135 may be a high efficiency particulate air (HEPA) filter for filtering the air received through the dirt collection unit 115. Other examples of the accessory filter 135 may include, but are not limited to, ultra-low penetration air (ULPA) filters, Micro Fresh filters, allergen filters, and carbon-activated filters.

In some embodiments, the cleaning unit 110 may be integrated with the airflow accessory 50 such as the fixed accessory and the wearable accessory. One having ordinary skill in the art would understand that when the cleaning unit 110 is integrated with the wearable accessory, only one of the first set of hoses and, a second set of hoses, which includes the second proximal hose 125 and the second distal hose 130, may be employed. Similar adjustments may be contemplated when integrating the cleaning unit 110 with the fixed accessory, e.g., the second distal hose 130 may be removed from the cleaning unit 110 and directly fitted to the unified airflow system through the airflow accessory 50. References to the airflow accessory 50 made hereinafter will refer to a configuration of the airflow accessory 50 which is integrated with the cleaning unit 110 for removing contaminants.

Further, each of the fixed accessory hose 75, the first proximal hose 85-1, and the second proximal hose 125, and/or with a hose extension kit, (collectively, set of proximal hoses) may enable an operator to effect cleaning within a reasonable radius depending on the airflow accessory 50 being mounted to or detached from the cabinet 20. Each hose in the set of proximal hoses may have a free-end configured for being coupled to one or more attachments such as an accessory attachment 140. Examples of the accessory attachment may include a nozzle, a brush, a hose, or any other suitable attachments known in the art, related art, or developed later. In some embodiments, the set of proximal hoses may be configured to suitably manipulate the fluid passage therethrough to increase or decrease the speed or, pressure of a passing fluid such as air based on the Bernoulli's principle. In some other embodiments, the airflow accessory 50 may be a standalone vacuum cleaner which may be configured to operate in tandem with an airflow from the unified airflow system 40. In further embodiments, the set of proximal hoses may include a UV source (not shown) projecting pulsed-UV light of suitable pulse characteristics such as those mentioned above for an, intended purpose including, but not limited to, disinfection, curing, and sintering.

Other embodiments of the airflow accessory 50 or the cleaning unit 110 may be, additionally or alternatively, adapted for odor removal. For example, the airflow accessory 50 may include a first compartment in flow communication with or storing a reactive agent and a second compartment in flow communication with the unified airflow system 40. Examples of the reactive agent may include, but not limited to, chemical agents (e.g., alcohols, aldehydes, oxidizing agents, naturally occurring or modified compounds, etc.), physical agents (e.g., heat, pressure, vibration, sound, radiation plasma, electricity, etc.), and biological agents (e.g., living organisms, plants or plant products, organic residues, etc.). Upon receiving a trigger from a control box such as a control unit 150 of the UVD device 10, the airflow accessory 50 may operate the first compartment to controllably release the reactive agent for being mixed with a fluid such as air passing through the second compartment. The trigger may be any mechanical, chemical, electrical stimuli, or any combination thereof, capable of manipulating the first compartment to controllably release the reactive agent. Alternatively, the second compartment may be triggered to selectively combine the fluid such as air with the reactive agent in the first compartment. The trigger may be provided manually by an operator or automatically effected by the control unit 150 upon predefined or dynamically conditions such intended concentration of the reactive agent in the fluid. The mix of fluid and reactive agent may be released into the unified airflow system 40 or out of the airflow accessory 50 via a proximal hose such as the set of proximal hoses depending on a respective negative pressure or a positive pressure of airflow in the airflow accessory 50. In some embodiments, the airflow accessory 50 such as a standalone vacuum cleaner may be configured to operate in, tandem with the unified airflow system 40.

Figure 16:
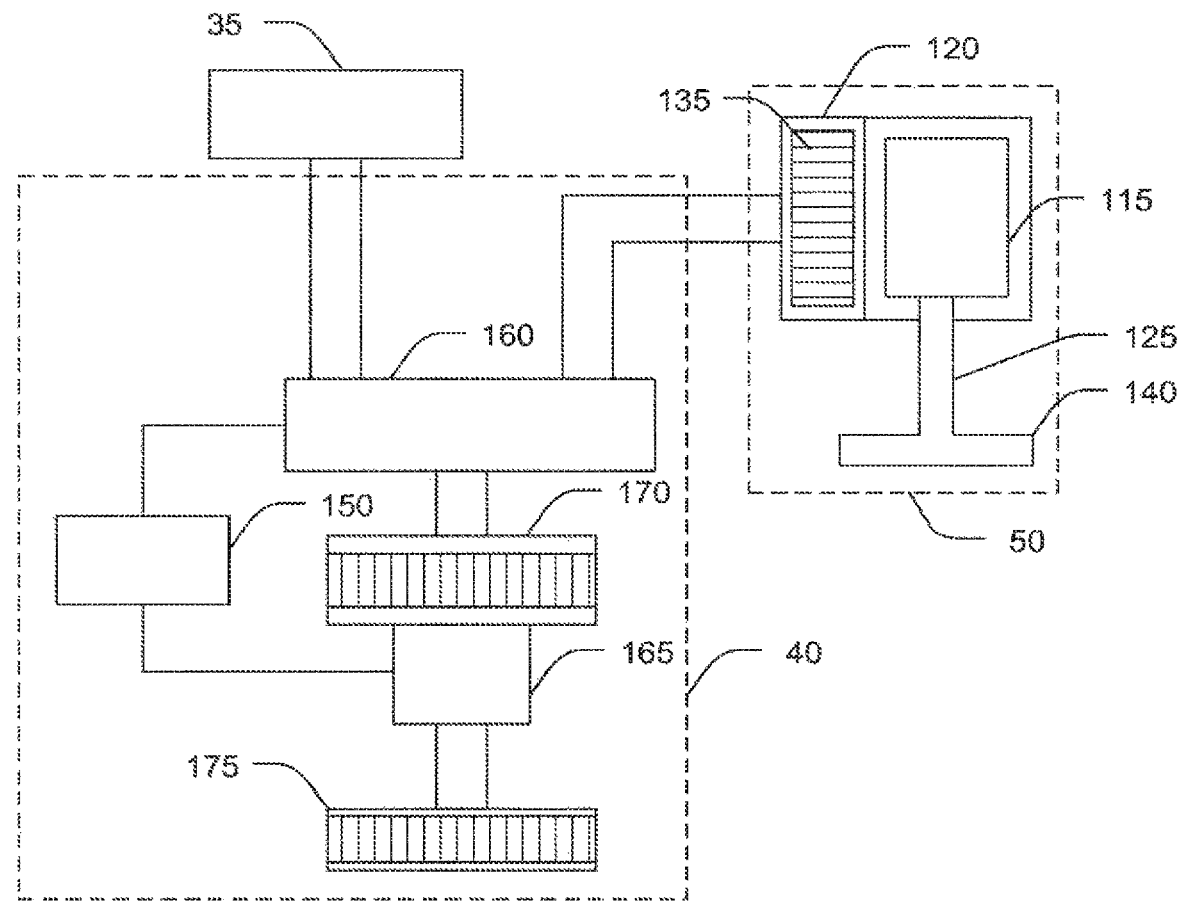
FIG. 16 illustrates a block diagram of an exemplary implementation of the unified airflow system of FIG. 1 with the area UV disinfection device of FIG. 1, according to an embodiment of the present disclosure.

As illustrated in FIG. 16, in one embodiment, the unified airflow system 40 may be implemented in flow communication with the UV lamp 35 and any suitable fluid management device, such as the airflow accessory 50, compatible with the unified airflow system 40; however, the airflow accessory 50 and the UV lamp 35 may be kept fluidically disconnected from each other. The airflow accessory 50 may have any suitable configurations known in the art, related art, or developed later including the fixed accessory and the wearable accessory. In one embodiment, the unified airflow system 40 may include a unified airflow assembly 145, the control unit 150, and a power supply unit 155. The control unit 150 may be any electronic or an electromechanical system configured to control predefined or dynamically defined functions and movements of various components including, but not limited to, the unified airflow assembly 145, the mobile carriage 15, the head assembly 30, the UV lamp 35, the motor, and the motorized tilt mechanism 62. In some embodiments, the control unit 150 may include or be implemented by way of a single device (e.g., a computing device, processor or an electronic storage device) or a combination of multiple devices. The control unit 150 may be implemented in hardware or a suitable combination of hardware and software. The "hardware" may comprise a combination of discrete electronic or electromechanical components, an integrated circuit, an application-specific integrated circuit, a field programmable gate array, a digital signal processor, or other suitable hardware. The "software" may comprise one or more objects, agents, threads, lines of code, subroutines, separate software applications, two or more lines of code or other suitable software structures operating in one or more software applications. The control unit 150 and the unified airflow assembly 145 as well as various components of the UVD device 10 may be powered by the power supply unit 155 including any source of high voltage power supply known in the art, related art, or developed later. Examples of the power supply unit 155 may include, but not limited to, a set of one or more batteries placed on the chassis 180 and an external electrical outlet via a power cord, which may be stored on a retractable reel disposed inside the cabinet 20.

The unified airflow assembly 145 configured to selectively decontaminate regions internal and external to the UVD device 10 via a shared air path. The unified airflow assembly 145 may include an airflow regulator 160, a vacuum pump 165, and one or more filters. The airflow regulator 160 may be configured regulate a flow communication between the vacuum pump 165 and other sites in response to a trigger from the control unit 150. For example, the airflow regulator 160 may regulate a flow communication between the vacuum pump 165 and the UV lamp 35 mutually exclusive to that between the vacuum pump 165 and the airflow accessory 50. In some embodiments, the unified airflow assembly 145 may be adapted to prevent any fluid communication between a site proximate to the UV lamp 35 and any other site located internal or external to the UVD device 10. The airflow regulator 160 may communicate with the vacuum pump 165 via a filtration compartment 170 including one or more filters to remove contaminants from a passing fluid such as air. The vacuum pump 165 may be connected to a discharge outlet to direct and discard incoming air from the UV lamp 35 or the airflow accessory 50. The discharge outlet may direct the incoming air through a gas filter 175 before discharging the air into the ambient surrounding. This gas filter 175 may prevent left-over or fluidic contaminants such as unwanted gases such as ozone in the incoming air from being released into the ambient surroundings. Various aspects of the unified airflow system 40 and, configurations of the unified, airflow assembly 145 are described below in detail with respect to the UVD device 10 of FIGS. 1-5.

As illustrated in FIGS. 17-20, the unified airflow system 40 may be mounted on a chassis 180 of the UVD device 10, where the chassis 180 may be attached to and supported by the mobile carriage 15. Although components particularly pertaining to implement the unified airflow system 40 are illustrated, one having ordinary skill in the art would understand other components pertaining to various functionalities of the UVD device 10 may be mounted on the chassis 180.

In one embodiment (FIG. 17), the unified airflow system 40 including the control unit 150, the power supply unit 155, and the unified airflow assembly 145 may be mounted on the chassis 180. In one example, the power supply unit 155 and the control unit 150 may be mounted on a lower section of the chassis 180 supported by the mobile carriage 15. Such positioning of the power supply unit 155 and the control unit 150 may assist to balance the weight of the UVD device 10 during movement, and maneuvers: however, other suitable positions or orientations may also be contemplated. The control unit 150 may be configured to operate the UVD device 10 in one or more predefined modes such as a disinfection mode and a cleaning mode; however, one having ordinary skill in the art may contemplate to define and implement additional operational modes for the UVD device 10 or any of the components associated therewith.

In the disinfection mode, the control unit 150 may be configured to drive the unified airflow assembly 145 for establishing a fluid, communication with the UV lamp 35 for removing hot air containing ozone around the UV lamp 35 while restricting airflow to/from the airflow accessory 50. In some embodiments, the control unit 150 may additionally disable the cleaning unit 110 during the disinfection mode. In the cleaning mode, the control unit 150 may be configured to drive the unified airflow assembly 145 to establish a fluid communication with the airflow accessory 50 for extracting contaminants such as dirt and debris from a target surface while restricting the fluid continuity to the UV lamp 35. In, some embodiments, the control unit 150 may additionally disable the UV lamp 35 during the cleaning mode. The operator may select one of these modes either through an input device such as the display unit 45 implemented as an interactive display screen, which may be configured to operate in communication with the control unit 150. Other examples of the input device may include, but are not limited to, a smartcard, a microphone, a stylus pen, a keyboard, a camera, a switch, a rotary knob, a computing device, or any other input device known in the art, related, or developed later. Alternatively, the operator may select these modes remotely using a computing device such as those mentioned above in communication with the control unit 150 over the network.

Figure 18:
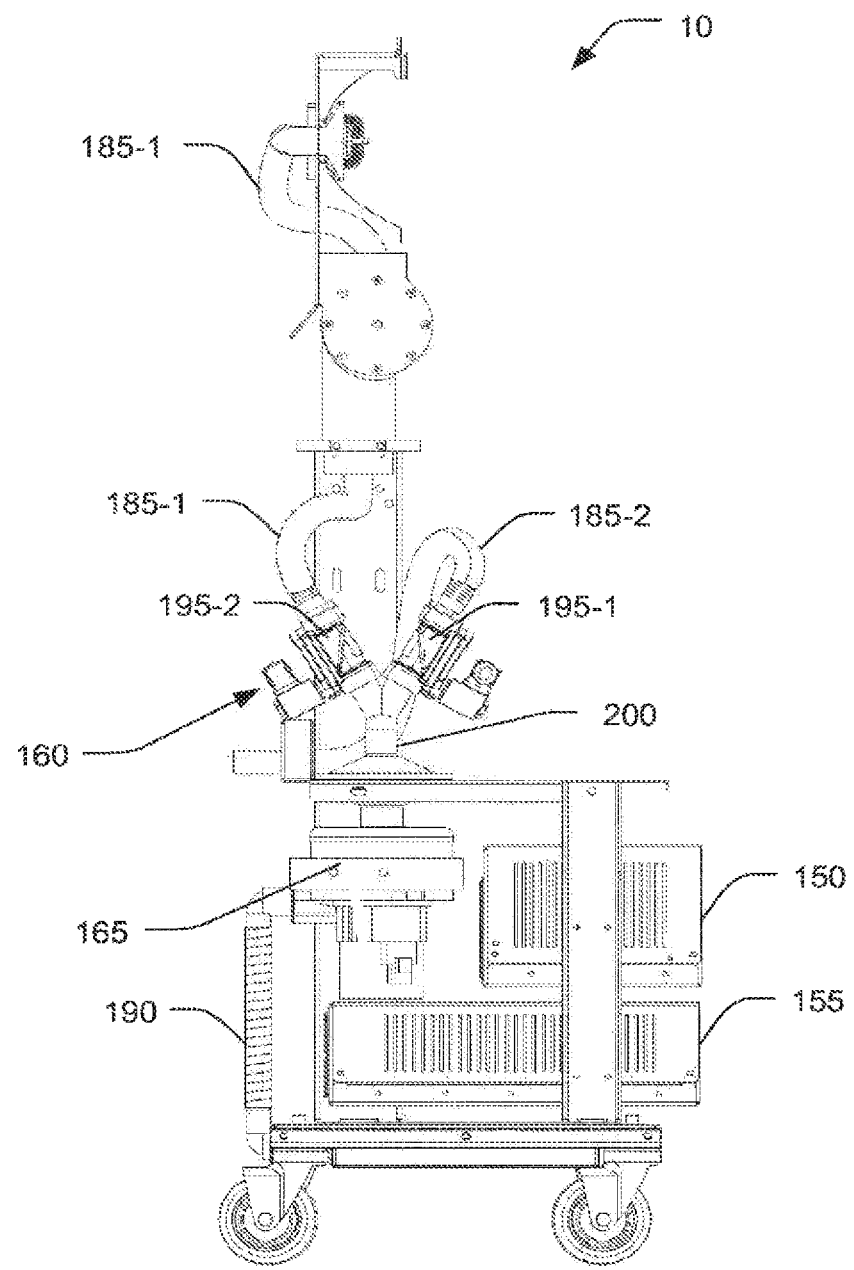
FIG. 18 is a left-side elevation view of the unified airflow assembly of FIG. 17, according to an embodiment of the present disclosure.

As shown in FIG. 18, the unified airflow assembly 145 may have various components including the airflow regulator 160, a UV hose 185-1 and an accessory hose 185-2

(collectively hoses 185), the vacuum pump 165, and a discharge hose 190 providing the discharge outlet. Each of these components may be manufactured separately and then assembled together. Alternatively, each of the hoses 185 may be integrated with the airflow regulator 160 to create a first part, which may be manufactured as a single unit. Similarly, the vacuum pump 165 may be integrated with the discharge hose 190 to create a second part, which may be manufactured as a single unit. The first part may then be detachably coupled to the second part for forming the unified airflow assembly 145. Such modular approach to removably assembling various components of the unified airflow assembly 145 may allow for easy replacement in case of any of these components become faulty. The airflow regulator 160 coupled to the hoses may be positioned on a top shelf of the chassis 180, e.g., above the control unit 150 and the power supply unit 155, for easy connectivity with predetermined sites.

The airflow regulator 160 may be configured to selectively regulate an airflow between the vacuum pump 165 and a predetermined site, e.g., the cleaning unit 110, relative to another site such as the head assembly 30 including the UV lamp 35. The airflow regulator 160 may be made of a single-piece or multiple pieces assembled together to create a substantially hollow regulator body including multiple openings and one or more air restriction units, which may toggle the airflow through each of those openings between the UV lamp 35 and the airflow accessory 50. In some embodiments, the number of openings may be based on the number of sites to be fluidically connected to the vacuum pump 165 or the number of shared fluid paths. The regulator body may have a variety of shapes, configurations, and dimensions suitable for the airflow regulator 160 to be (i) secured at a predetermined location within the UVD device 10, and (ii) create a predetermined amount of air pressure at the openings and in the hoses connected or coupled to those openings of the airflow regulator 160. The regulator body may be made up of any suitable material configured to withstand a predetermined amount of pressure and temperature that may develop inside or outside the airflow regulator 160. Exemplary materials for the body may be rigid, flexible, or semi-rigid materials including, but not limited to, metals, polymers, composites, alloys, or any other suitable material known in the art, related art, or developed later.

First Configuration of the Airflow Regulator

Figure 17:
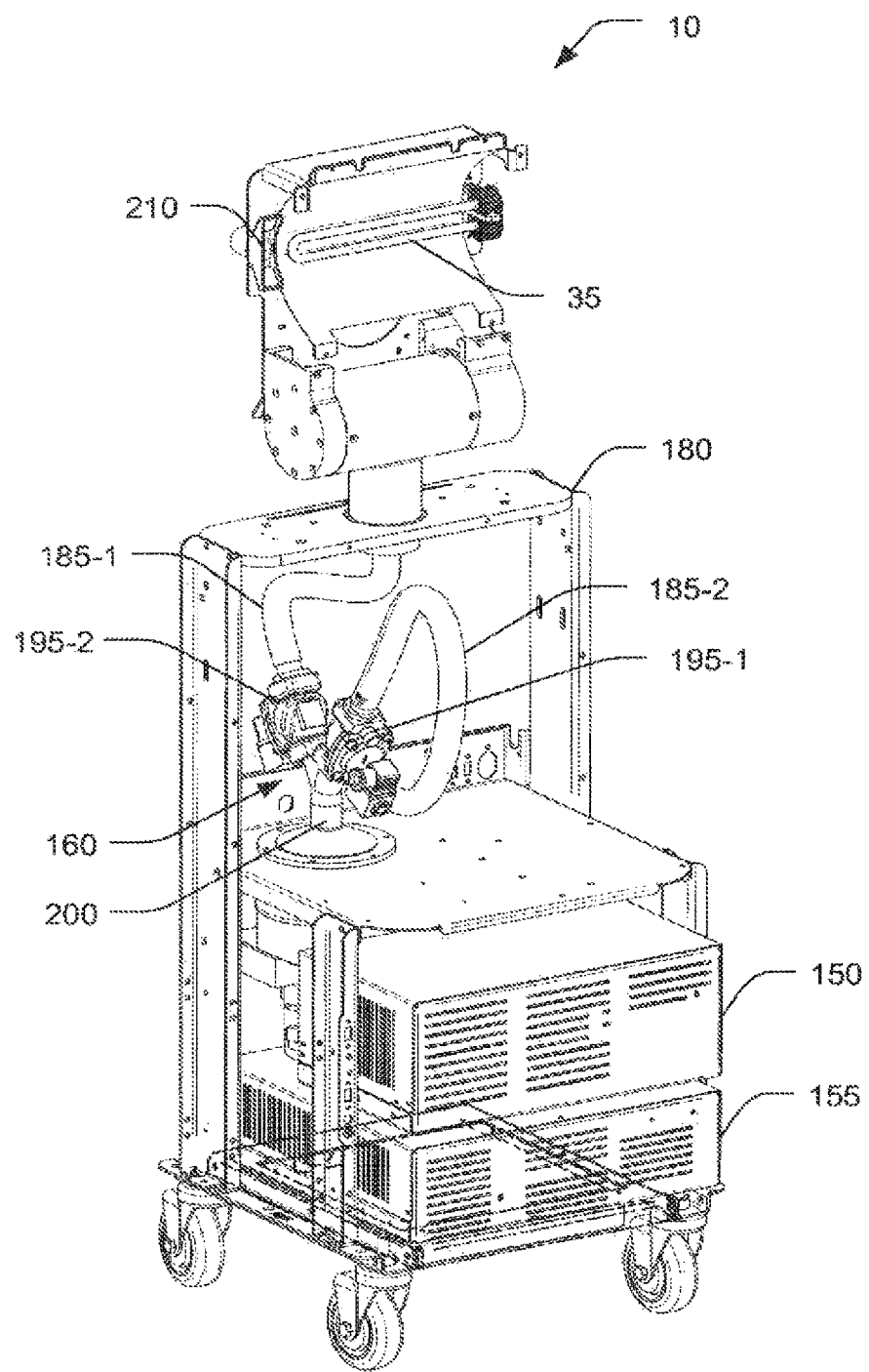
FIG. 17 is a front isometric view of a first configuration of an exemplary unified airflow assembly for the unified airflow system of FIG. 16 illustrating the unified airflow assembly mounted on a chassis of the area UV disinfection device of FIG. 1, according to an embodiment of the present disclosure.
Figure 21:
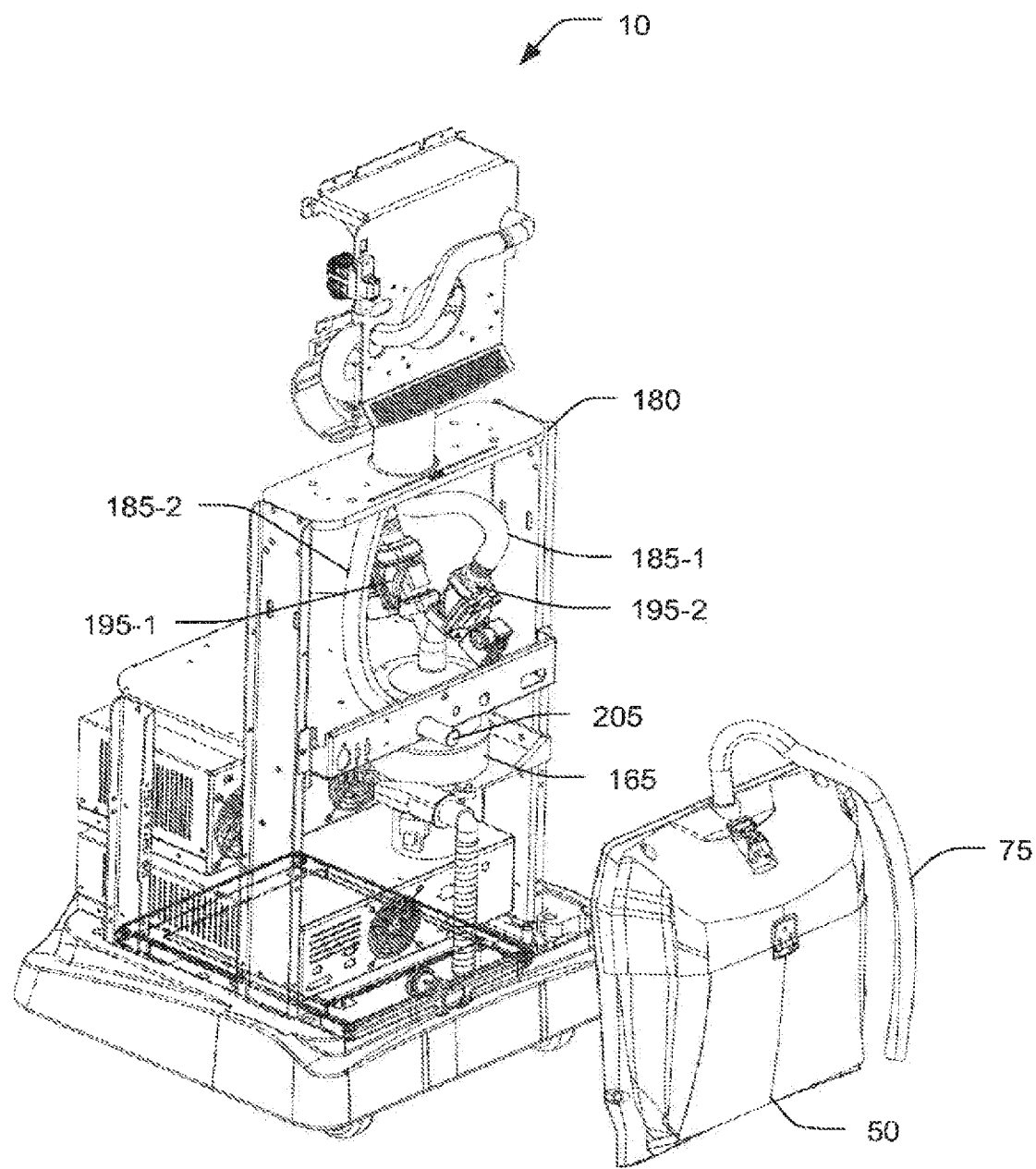
FIG. 21 is a rear isometric view of the unified airflow assembly of FIG. 17 illustrating the fixed airflow accessory of FIG. 6, according to an embodiment of the present disclosure.

The airflow regulator 160 may have any suitable configurations based on the number of sites to be decontaminated and the desired number of shared fluid paths. For example, in a first configuration (FIGS. 17-19), the airflow regulator 160 may have a substantially Y-configuration for being fluidically connected to two predetermined sites such as the head assembly 30 and an airflow accessory 50. The airflow regulator 160 may have a substantially Y-shaped, rigid, hollow body including a first side arm 195-1, a second side arm 195-2 (collectively referred to as side arms 195), and a central arm 200. The first side arm 195-1 may be at a predetermined angle with respect to the second side arm 195-2. In one example, the first side arm 195-1 may be perpendicular to the second side arm 195-2. In another example, an angle between the side arms 195 may be less than, ninety degrees. The first side arm 195-1 may be coupled to the accessory hose 185-2, which may have a first open end 205 extending to the rear side of the UVD device 10. The first open end 205 may be secured to a portion of the chassis 180 or the mobile carriage 15 for easy connection with a connectable accessory. For example (FIG. 21), the fixed accessory may include an opening (not shown) for being coupled to the accessory hose 185-2 via the first open end 205 using any suitable connection mechanisms. Examples of the connection mechanisms may include, but not limited to, welding, molding, a snap fit, a screw fit, a liter-lock, and gluing, which may be chosen depending on the materials from which the fixed accessory may be made. Similarly, the accessory hose 185-2 may be coupled to the first, distal hose 85-2 of the wearable accessory or the second distal hose 130 of the cleaning unit 110. On the other hand, the second side arm 195-2 may be coupled to the UV hose 185-1, which may extend to the head assembly 30 (FIG. 20) and have a second open end 210 proximate to the UV lamp 35 (FIG. 17). In some embodiments, the first open end 205 may be coupled to a set of multiple hoses or a single hose having multiple openings (not shown) attached to the mobile carriage 15 and oriented towards the floor.

Figure 19:
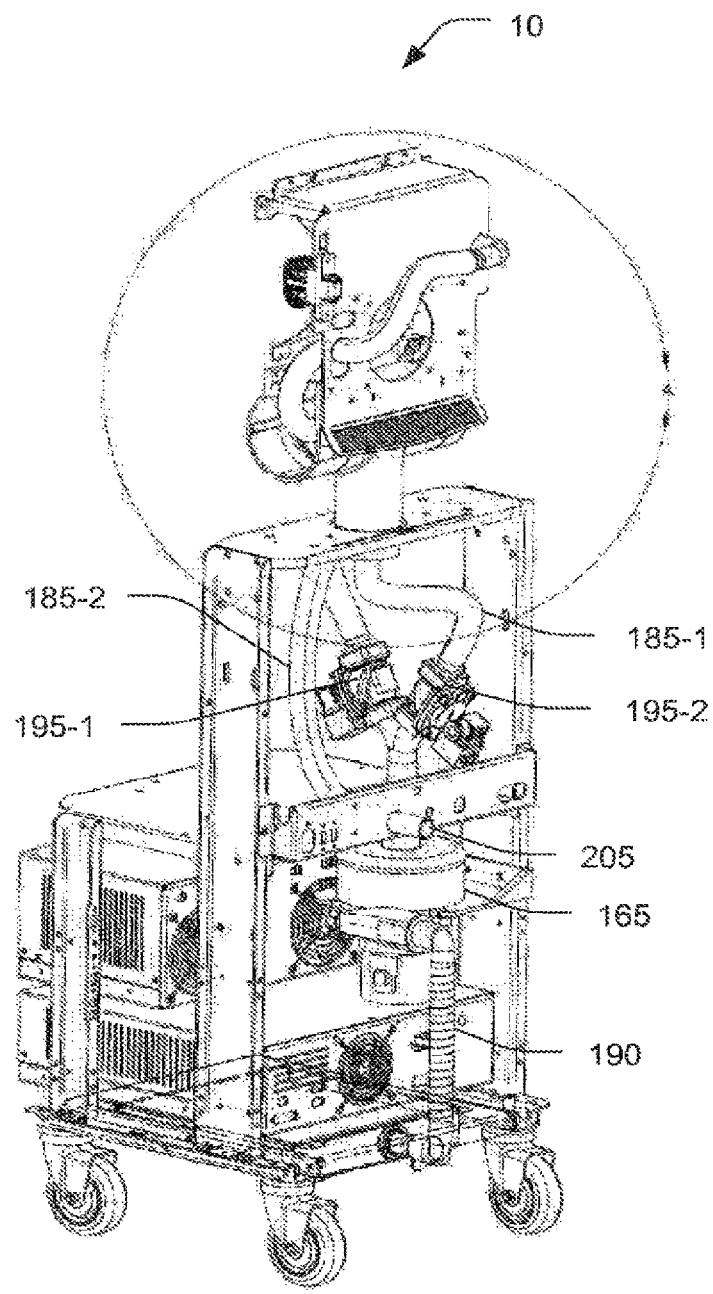
FIG. 19 is a rear isometric view of an exemplary unified airflow assembly of FIG. 17 mounted on the area UV disinfection device of FIG. 1, according to an embodiment of the present disclosure.
Figure 20:
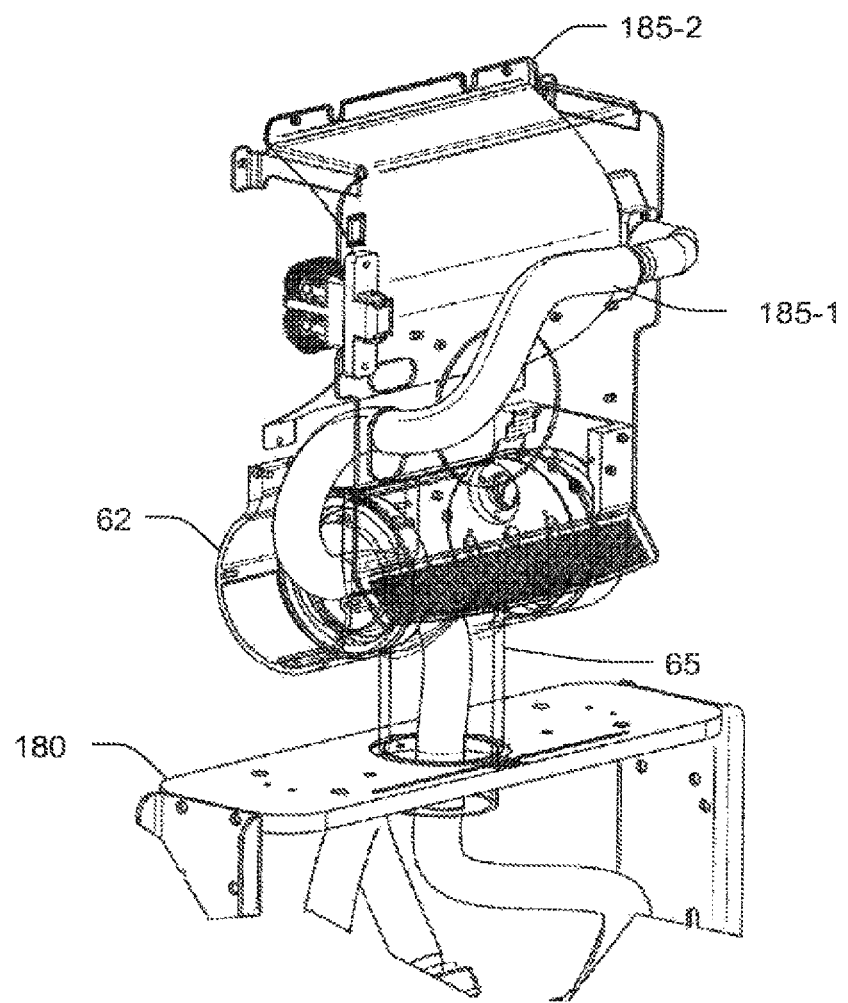
FIG. 20 is a rear isometric view of the head assembly of the area UV disinfection device of FIG. 1 without the cabinet taken along the circle A of FIG. 19, according to an embodiment of the present disclosure.

Further, as shown in FIG. 19, the unified airflow assembly 145 may include the vacuum pump 165, whose one end may be coupled to the airflow regulator 160 from under the top shelf and the other end may be, coupled to the discharge hose 190. The vacuum pump 165 may be of any suitable type known in the art, related art, or developed later. Examples of the vacuum pump 165 include, but are not limited to, a flow-through pump, a peripheral bypass pump, and a tangential bypass pump. The discharge hose 190 may extend from the vacuum pump 165 for being coupled to the mobile carriage 15 via one or more filters Configured absorb reactive gases. In one embodiment, the unified airflow assembly 145 may include a gas filter 175 interfacing between the discharge hose 190 and the mobile carriage 15 for absorbing the harmful ozone gas in the hot air produced proximate to the UV lamp 35 due to heating-up of the UV lamp 35 during operation. Examples of the gas filter 175 may include, but not limited to, a charcoal filter, an activated-carbon filter, or any other suitable gas filter 175 known in the art, related art, or developed later depending on a desired gas to be filtered or removed.

In some embodiments, the vacuum pump 165 may be configured to operate in different modes implemented by the control unit 150. For example, the vacuum pump 165 may be configured to operate in a power mode and a blower mode. In the power mode, the control unit 150 may be configured to modify aspects of the vacuum pump 165 for manipulating the suction capacity thereof or the pressure per unit time of the fluid such as air driven or passing therethrough. For example, the control unit 150 may increase the voltage or current applied to the vacuum pump 165, in accordance with the manufacturer's specification, to increase the speed of rotation of the vacuum pump 165, thereby increasing the suction capacity, and vice versa. In the blower mode, the control unit 150 may reverse the polarity of the voltage or current applied to the vacuum pump 165, thereby changing the direction of rotation of the vacuum pump 165 to create a positive air pressure instead of a negative air pressure in the airflow regulator 160. One having ordinary skill in the art would understand that the blower mode may be implemented provided the vacuum pump 165 is a reversible vacuum pump 165. Further, in some embodiments, the control unit 150 may be configured to drive the unified airflow assembly 145 to block airflow to the UV hose 185-1 in the blower mode.

Figure 22:
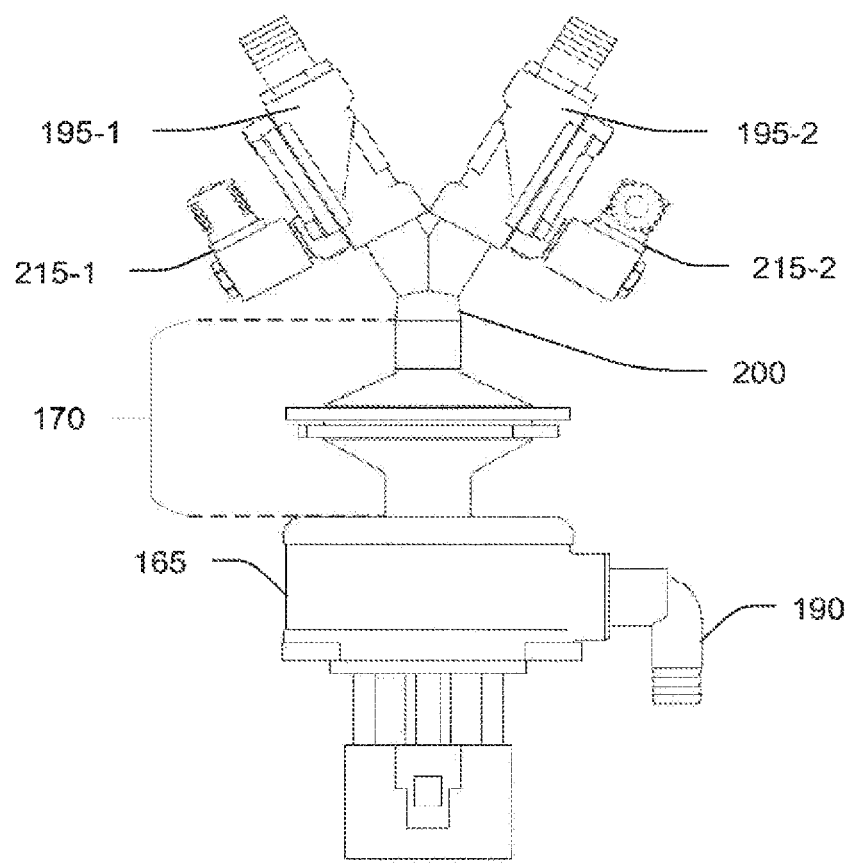
FIG. 22 is a right-side elevation view of the unified airflow assembly of FIG. 17 removed from the chassis, according to an embodiment of the present disclosure.
Figure 23:
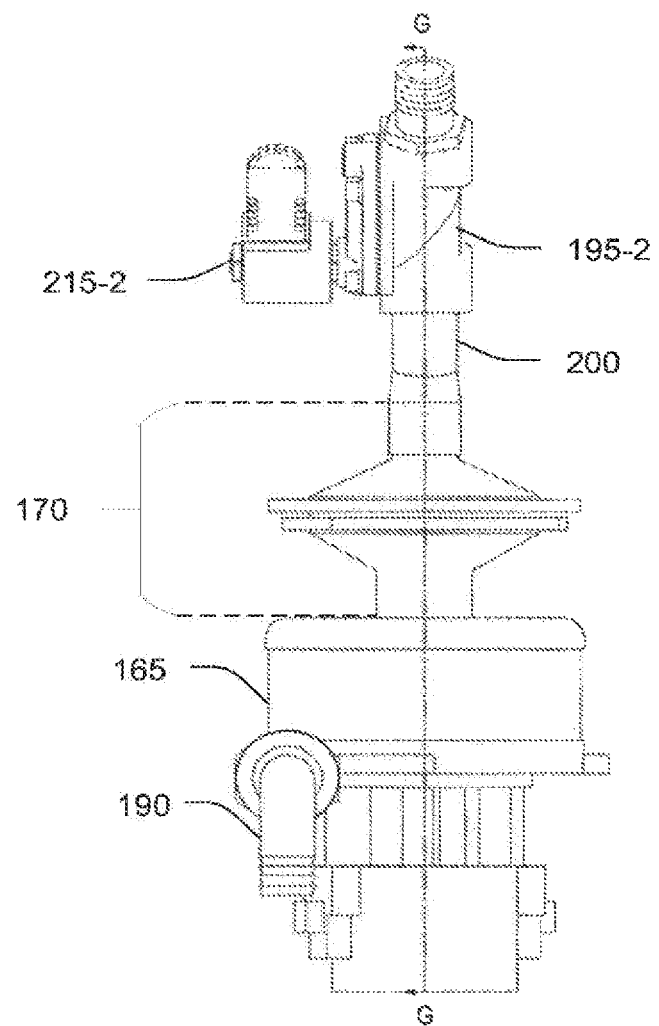
FIG. 23 is a rear elevation view of the unified airflow assembly of FIG. 22, according to an embodiment of the present disclosure.

As shown in FIG. 22, the body of the Y-shaped airflow regulator 160 may include a first Y-air restriction unit 215-1 and a second Y-air restriction unit 215-2 (collectively, Y-air restriction units 215). The first Y-air restriction unit 215-1 may be coupled to the first side arm 195-1 and the second Y-air restriction unit 215-2 may be coupled to the second side arm 195-2 of the Y-shaped airflow regulator 160. The first Y-air restriction unit 215-1 may be configured to control the flow communication between the vacuum pump 165 and the airflow accessory 50, and the second Y-air restriction unit 215-2 may be configured to control the flow communication between the vacuum pump 165 and the UV lamp 35, or the head assembly 30. Exemplary designs for the Y-air restriction units 215 may include, but not limited to, valves, plugs, discs, or any other suitable designs known in the art, related art, or developed later. In one embodiment, each of the air restriction units 215 may be implemented as solenoid valves operating to selectively restrict a fluid path. For example (FIG. 24), a first solenoid valve 220-1 may be located within the first side arm 195-1 to restrict the airflow through the accessory hose 185-2 and a second solenoid valve 220-2 may be located within the second side arm 195-2 to restrict the airflow through the UV hose 185-1. The first solenoid valve 220-1 is illustrated in a closed position and the second solenoid valve 220-2 is shown in an open position. Each of the first solenoid valve 220-1 and the second solenoid valve 220-2 (collectively, solenoid valves 220) may be configured to open mutually exclusive each other by the control unit 150.

Figure 24:
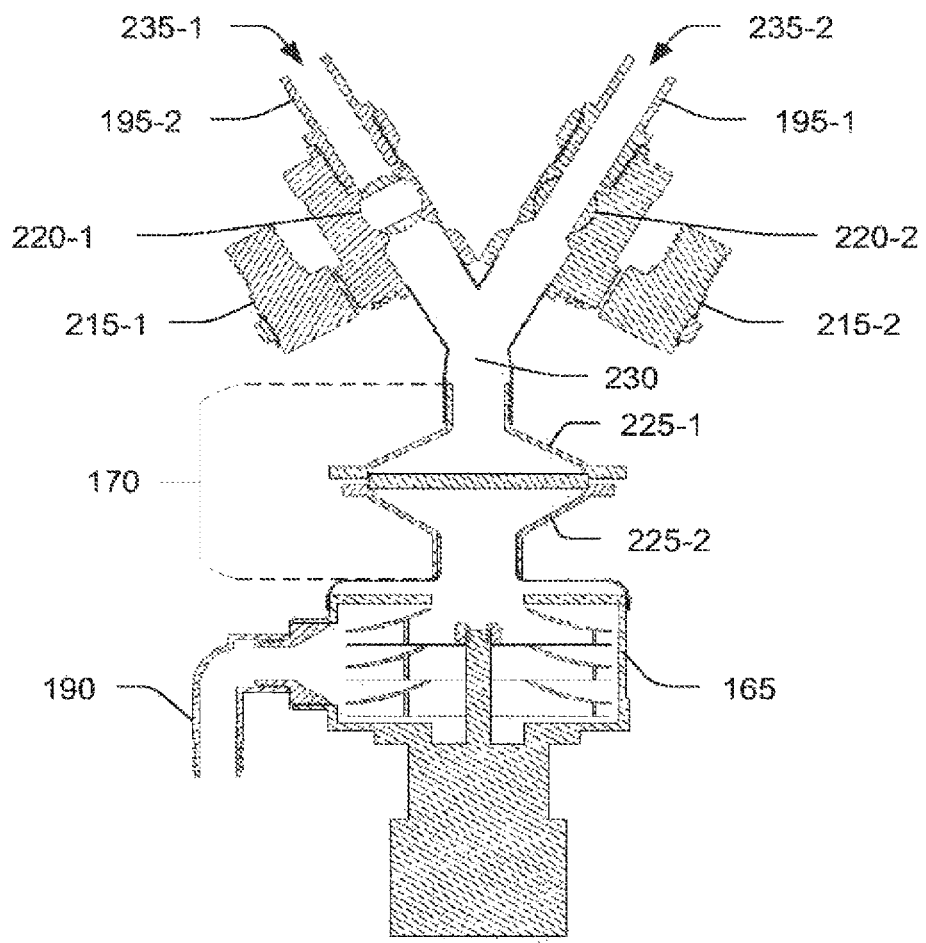
FIG. 24 is a cross-sectional view of the unified airflow assembly of FIG. 22 taken along the line G-G of FIG. 23, according to an embodiment of the present disclosure.

As shown in FIG. 24, the central arm 200 may extend to the filtration compartment 170 including a first chamber 225-1 and a second chamber 225-2 separated by a suitable filter such as those mentioned above. For example, the central arm 200 may be fluidically coupled to the first chamber 225-1. Similarly, the second chamber 225-2 may be fluidically coupled to the vacuum pump 165 directly or through a vacuum hose. Further, as shown in FIG. 24, the Y-regulator body of the Y-shaped airflow regulator 160 may include a main opening 230 and peripheral openings. The central arm 200 of the Y-shaped airflow regulator 160 may extend into the main opening 230 interfacing with the first chamber 225-1 of the filtration compartment 170. Similarly, the first side arm 195-1 may extend into a first peripheral opening 235-1 interfacing with the accessory hose 185-2 and the second side arm 195-2 may extend into a second peripheral opening 235-2 interfacing with the UV hose 185-1. The Y-air restriction units such as the solenoid valves 220 may be configured to control the flow communication, via the main opening 230, of the vacuum pump 165 with (1) the airflow accessory 50 via the first peripheral opening 235-1 and (2) the UV lamp 35 via the second peripheral opening 235-2. The first peripheral opening 235-1 and the second peripheral opening 235-2 are hereinafter collectively referred to as peripheral openings.

Second Configuration of the Airflow Regulator

Figure 25:
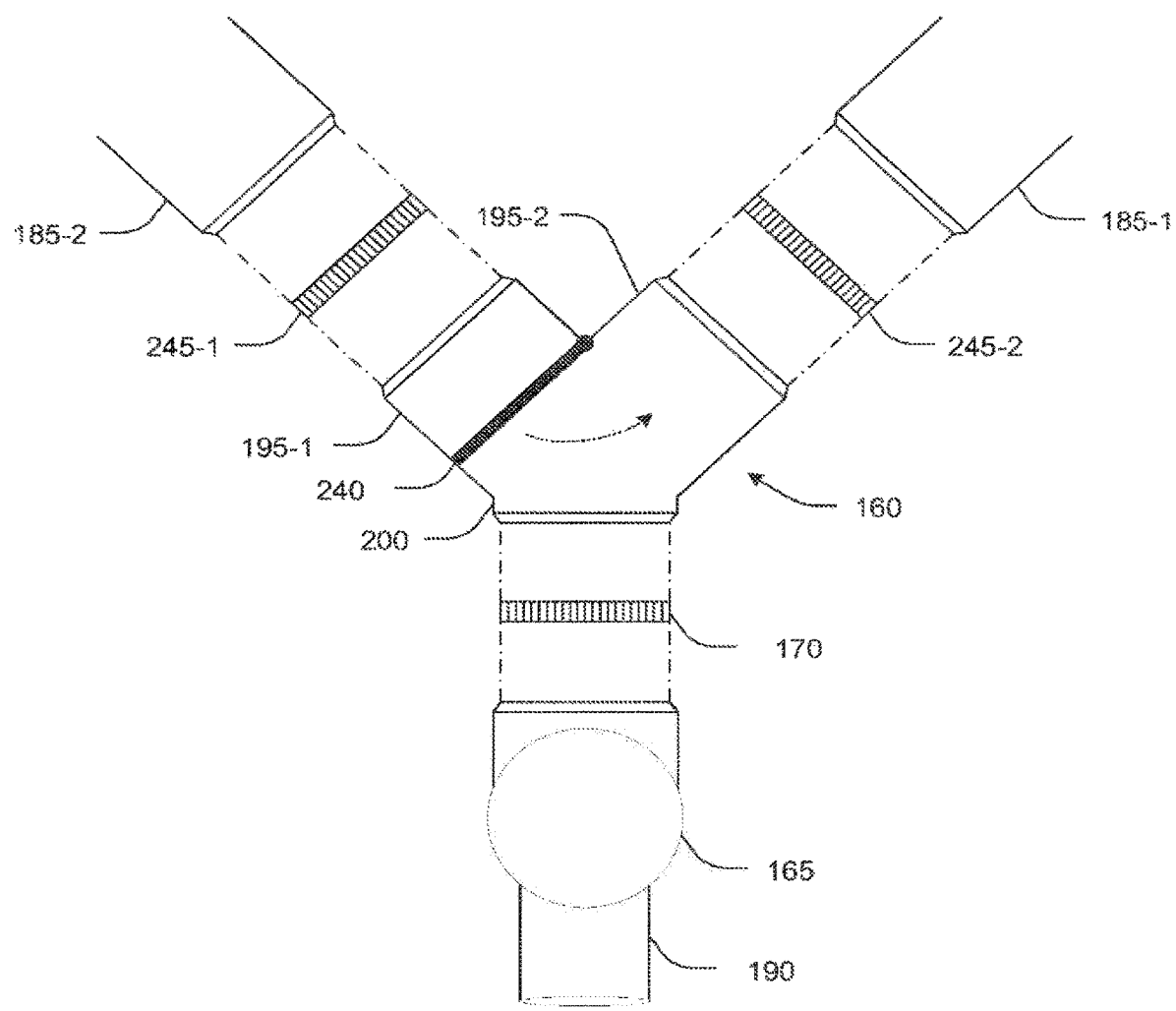
FIG. 25 is an exploded view of an exemplary second configuration of the unified airflow assembly of FIG. 16, according to an embodiment of the present disclosure.
Figure 26:
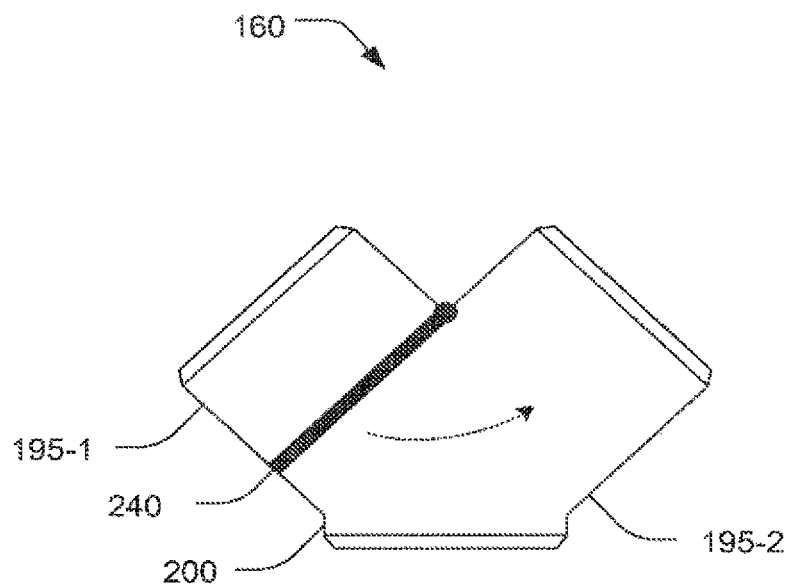
FIG. 26 is a schematic illustrating an exemplary airflow regulator for the unified airflow assembly of FIG. 25, according to an embodiment of the present disclosure.
Figure 27:
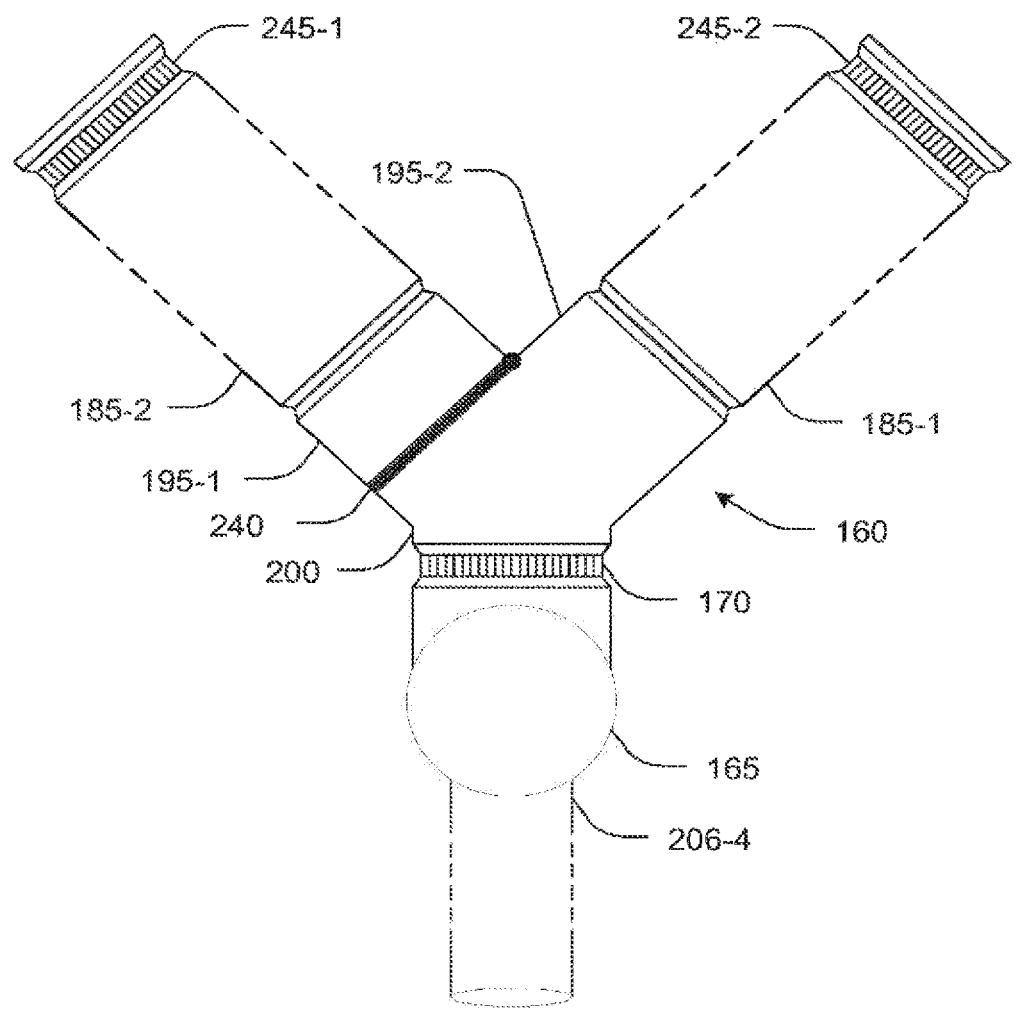
FIG. 27 is a schematic illustrating alternative configuration of the unified airflow assembly of FIG. 26, according to an embodiment of the present disclosure.

In a second configuration illustrated in FIGS. 25-27, the airflow regulator 160 may have a Y-shaped body including the side arms 195 and the central arm 200 similar to the first configuration; however (FIG. 25), the airflow regulator 160 may include a single air restriction unit 240, instead of two Y-air restriction units 215, movably connected at an intersection point of the first side arm 195-1 and the second side arm 195-2 within the Y-shaped airflow regulator 160. The side arms 195 may have a predetermined angle between them. The single air restriction unit 240 (or S-air restriction unit 240) may be configured to pivot about a horizontal axis extending across the intersection point. This S-air restriction unit 240 may pivot to substantially restrict the airflow through the first side arm 195-1 or the second side arm 195-2. For example, the S-air restriction unit 240 may pivot leftward to block the first side arm 195-1 and restrict the airflow therethrough while allowing the airflow through the second side arm 195-2. Alternatively, the S-air restriction unit 240 may pivot rightward to block the second side arm 195-2 and restrict the airflow therethrough while allowing the airflow through the first side arm 195-1. While the illustrated embodiments include the S-air restriction unit 240 pivoting to substantially block a predetermined air passage within the Y-shaped airflow regulator 160, one skilled in the art may contemplate other suitable movements including rotary, pan, swivel, tilt, extend, and slide based on the design of the S-air restriction unit 240. Exemplary designs of the S-air restriction unit 240 may include such as those mentioned above. Accordingly, such S-air restriction unit 240 may cause the airflow between the central arm 200 and the first side arm 195-1 to be mutually exclusive to the airflow between the central arm 200 and the second side arm 195-2.

The S-air restriction unit 240 may be controlled automatically or manually using a variety of mechanisms known in the art, related art, or developed later. Exemplary mechanisms may include, but not limited to, electronic/electrical, mechanical, or electromechanical actuation, or any combination thereof. For example, the S-air restriction unit 240 may be controlled by the control unit 150 to automatically pivot to block the first peripheral opening 235-1 when a human is present within a predetermined proximity to the UVD device 10. Further, in addition to the filtration compartment 170, a first hose filter 245-1 may be secured between the first side arm 195-1 and the accessory hose 185-2 and a second hose filter 245-2 may be secured between the second side arm 195-2 and the UV hose 185-1. Alternatively, as shown in FIG. 27, the first side arm 195-1 may directly secure a portion of the accessory hose 185-2, where the first hose filter 245-1 may be removably secured to the accessory hose 185-2. Similarly, the second side arm 195-2 may directly secure a portion of the UV hose 185-1 and the second hose filter 245-2 may be removably secured to the UV hose 185-1 or the first distal hose 85-2 of the airflow accessory 50, or the second distal hose 130 of the cleaning unit 110.

Third Configuration of the Airflow Regulator

Figure 28:
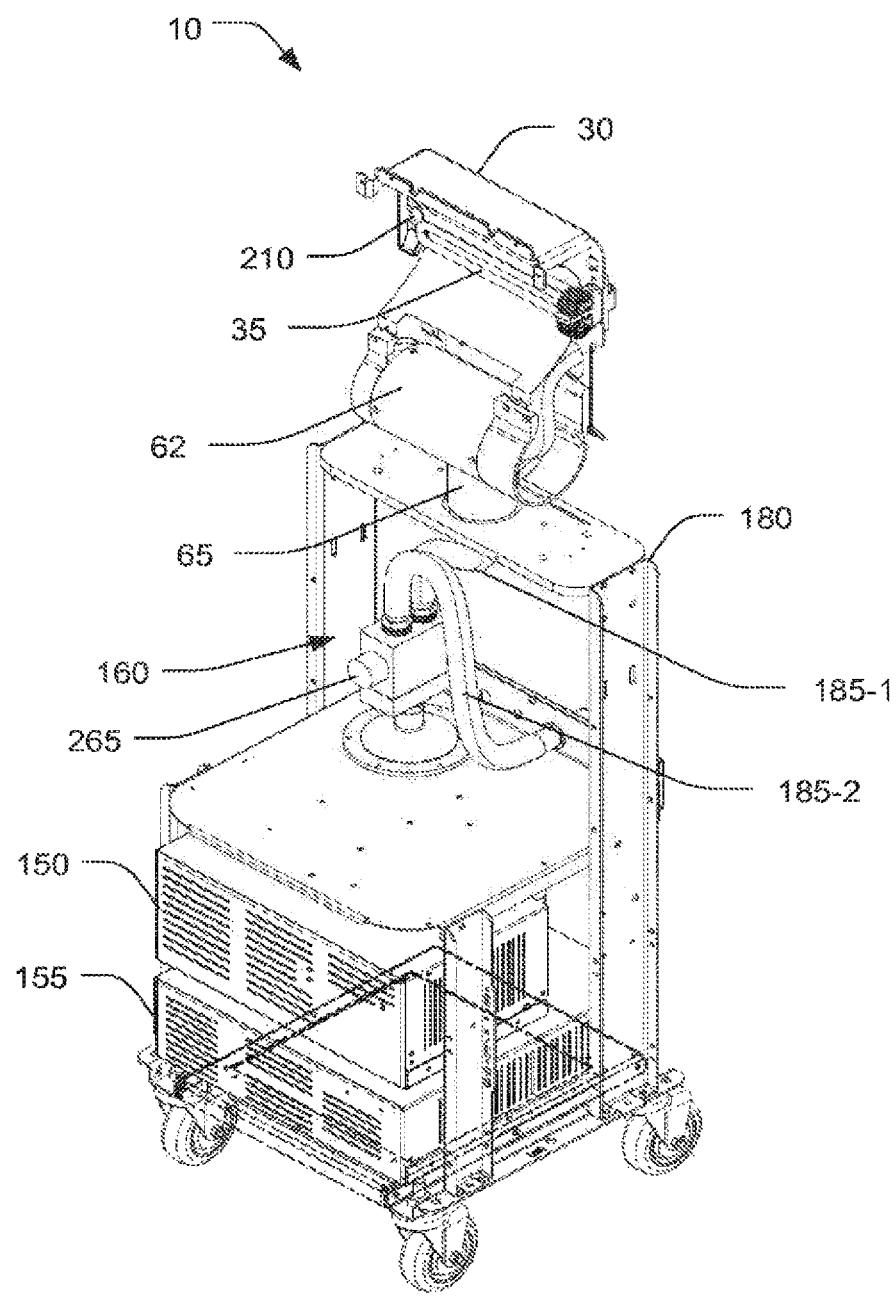
FIG. 28 is a front isometric view of an exemplary third configuration of the unified airflow assembly of FIG. 16 mounted on the chassis of the area UV disinfection device of FIG. 1, according to an embodiment of the present disclosure.
Figure 29:
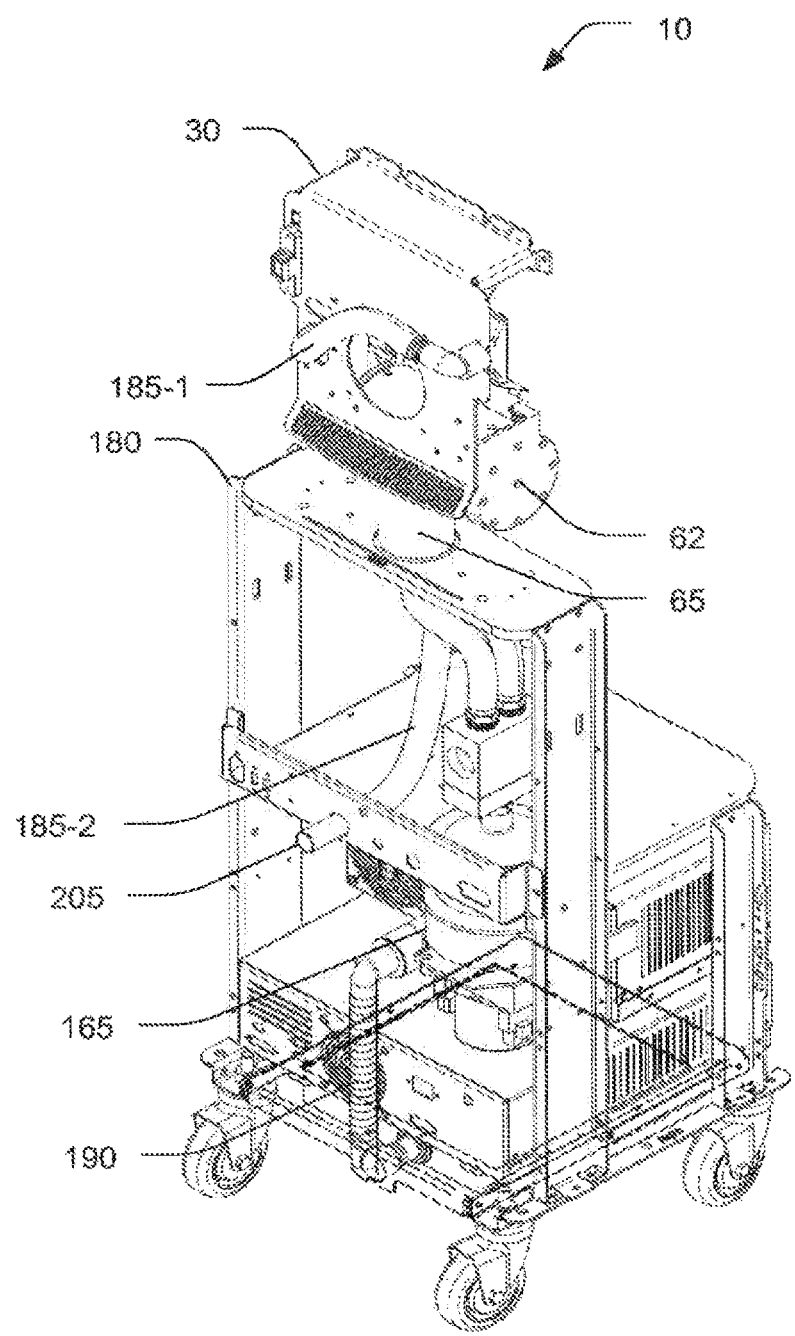
FIG. 29 is a rear isometric view of the unified airflow assembly of FIG. 28, according 10 an embodiment of the present disclosure.
Figure 30:
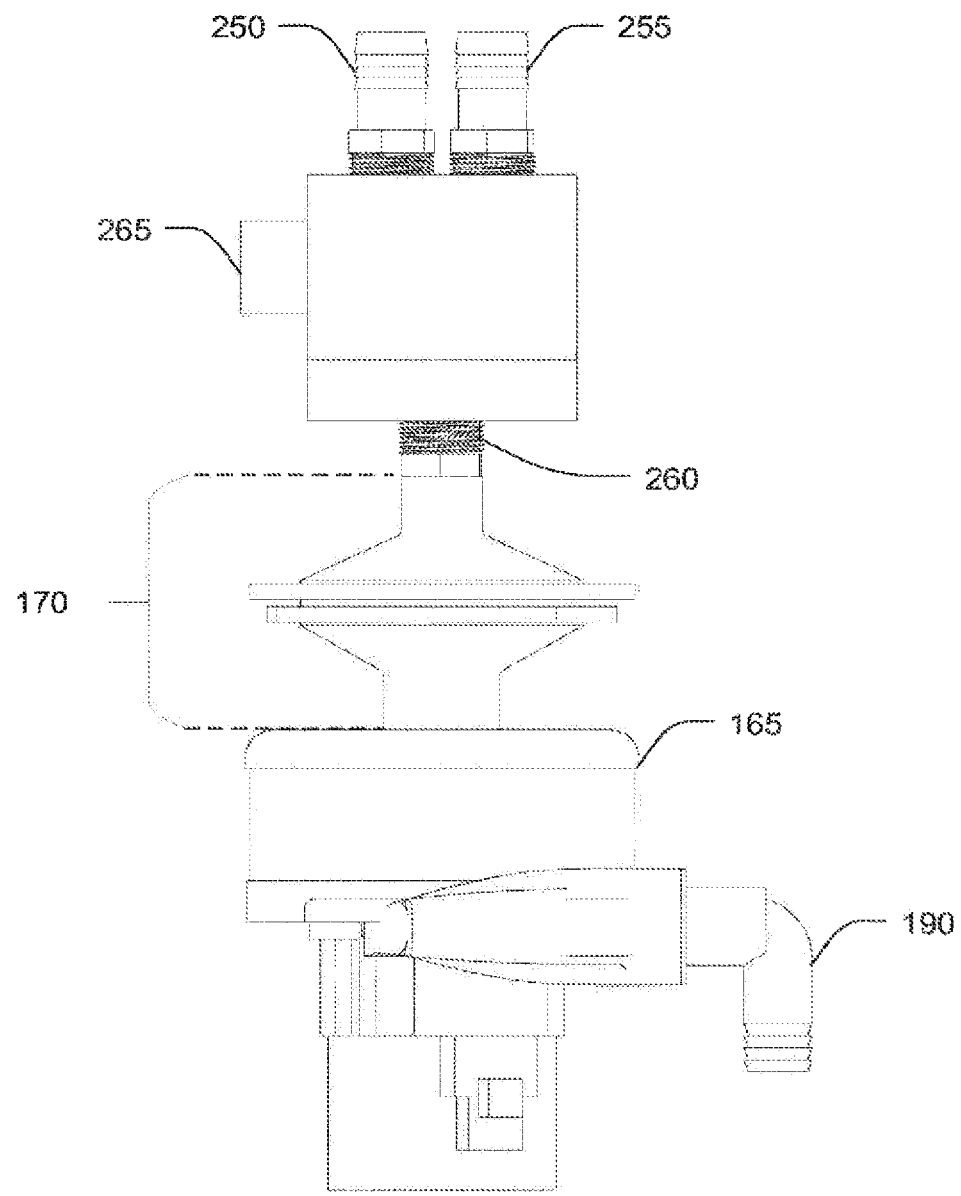
FIG. 30 is a right-side elevation view of the unified airflow assembly of FIG. 28 removed from the chassis, according to an embodiment of the present disclosure.

In a third configuration (FIGS. 28-29), the airflow regulator 160 may have a substantially U-configuration for being fluidically connected to two predetermined sites such as the UV lamp 35 (or the head assembly 30) and the airflow accessory 50. The airflow regulator 160 may have a U-shaped, rigid, body including a vacuum arm 260, a UV arm 255, and an accessory arm 250 (FIG. 30), which may be parallel to each other. Further, in one example, the accessory arm 250 and the UV arm 255 may be in the same plane. In another example, at least two of the vacuum arm 260, the UV arm 255, and the accessory arm 250 may be located in the same plane. In yet another example, the vacuum arm 260 may be in a plane different from those of the UV an 255 and the accessory arm 250.

Figure 31:
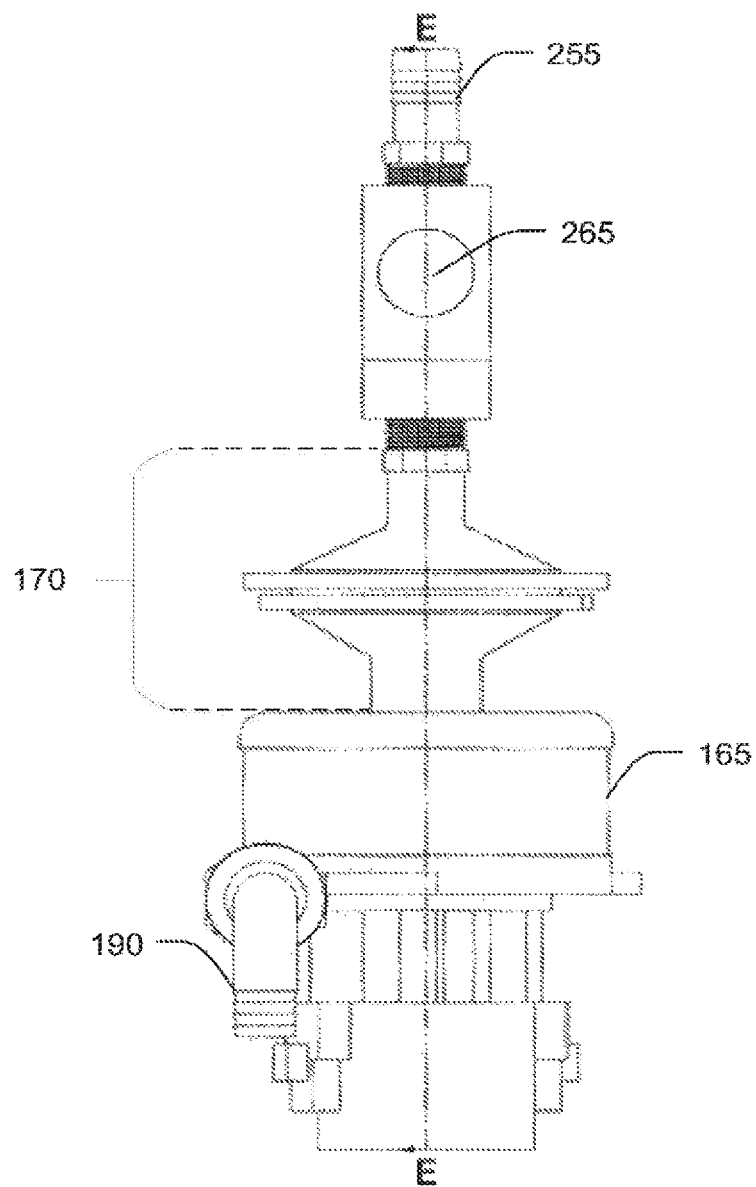
FIG. 31 is a rear elevation view of the unified airflow assembly of FIG. 30, according to an embodiment of the present disclosure.

The accessory arm 250 may be coupled to the accessory hose 185-2 extending 10 have the first open end 205 opening to the rear side of the UVD device 10. The first open end 205 may be secured to the chassis 180 for easy connection with a compatible accessory such as the airflow accessory 50. On the other hand, the UV arm 255 may be coupled to the UV hose 185-1, which may extend to the head assembly 30 (FIG. 29) and have the second open end 210 proximate to the UV lamp 35 (FIG. 28), Similar to the first configuration, the airflow regulator 160 may be vertically arranged with other components of the unified airflow assembly 145, such as the filtration compartment 170 and the vacuum pump 165, in the U-configuration (FIG. 31); however, other suitable arrangements may be contemplated. One having ordinary skill in the art would understand that the arrangement, position, design, and, functionalities of rest of the components including the vacuum pump 165, the discharge hose 190, and the filtration compartment 170 may be same as those described above in the description for FIGS. 17-20.

Figure 32:
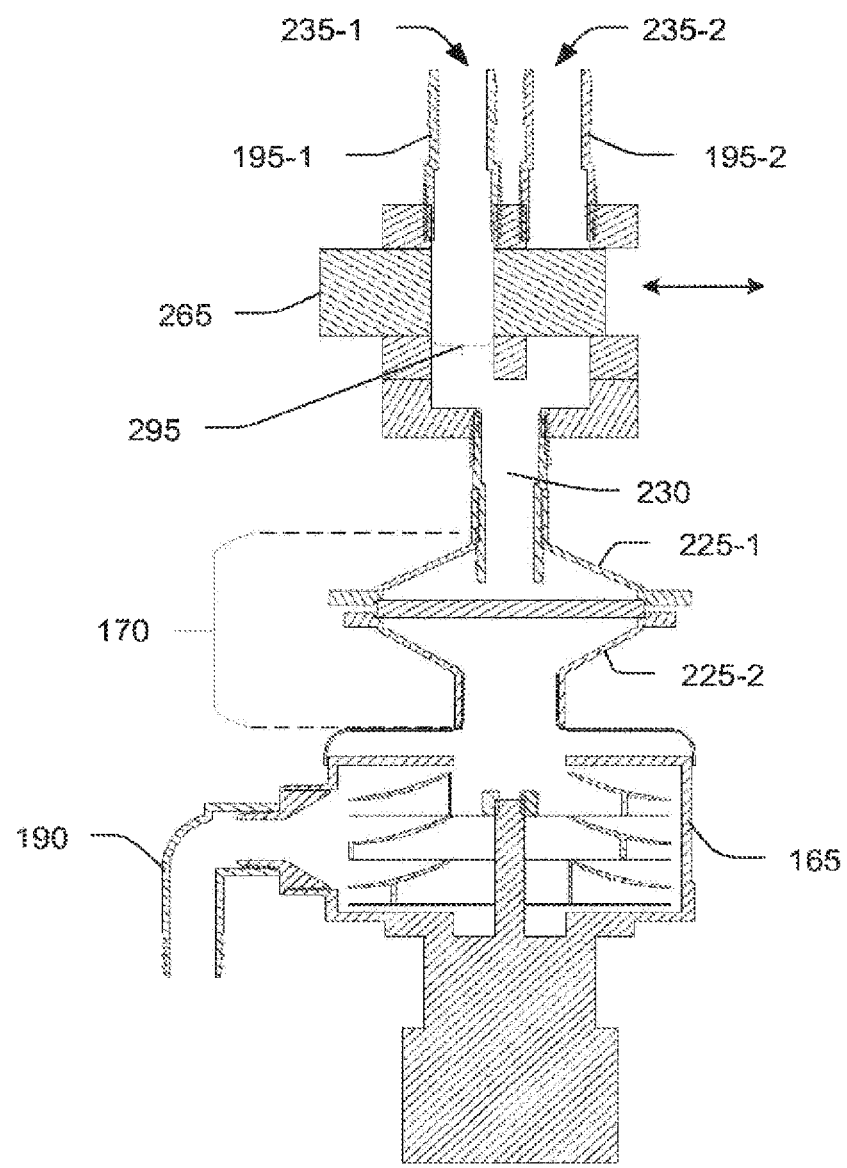
FIG. 32 is a cross-sectional view of the unified airflow assembly of FIG. 30 taken along the line E-E of FIG. 31, according to an embodiment of the present disclosure.

In one embodiment, as shown in FIG. 32, the U-shaped body of the airflow regulator 160 may include a single air restriction unit coupled to both the UV arm 255 and the accessory arm 250. The air restriction unit may be configured to selectively open a fluid path from the vacuum pump 165 either to the accessory arm 250 or the UP arm 255, thereby controlling the flow communication between the vacuum pump 165 and either the airflow accessory 50 or the UV lamp 35 respectively. In one embodiment, the air restriction unit may be a linear actuator valve 265 configured to transition back and forth to selectively restrict a fluid path. The actuator valve 265 may include gap 295 configured to align with a desired fluid path of either the accessory arm 250 or the UV arm 255 upon being triggered by the control unit 150. Such alignment may open the desired fluid path, e.g., of the accessory arm 250 or the UV arm 255, to allow a fluid flow therethrough at a given instance.

Similar to the first configuration, the body of the airflow regulator 160 may include the main opening 230 and the peripheral openings. The vacuum arm 260 of the airflow regulator 160 may extend into the main opening 230 interfacing with the first chamber 2254 of filtration compartment 170. Similarly, the accessory arm 250 may extend into the first peripheral opening 235-1 interfacing with the accessory hose 185-2, and the UV arm 255 may extend into the second peripheral opening 235-2 interfacing with the UV hose 185-1. The linear actuator valve 265 may be configured to control the flow communication, vita the main opening 230, of the vacuum pump 165 with (1) the airflow accessory 50 via the first, peripheral opening 235-1 and (2) the UV lamp 35 via the second peripheral opening 235-2. The first peripheral opening 235-1 and the second peripheral opening 235-2 are hereinafter collectively referred to as peripheral openings 235.

Fourth Configuration of the Airflow Regulator

Figure 33:
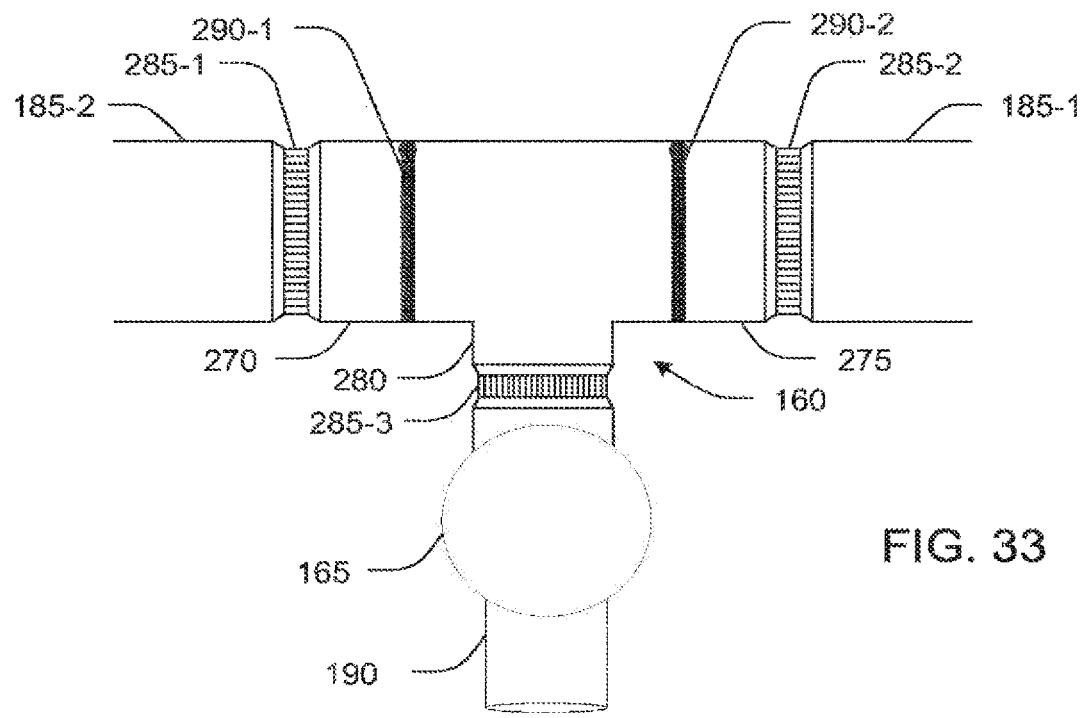
FIG. 33 is a schematic illustrating an exemplary fourth configuration of the unified airflow assembly of FIG. 16, according to an embodiment of the present disclosure.
Figure 34:
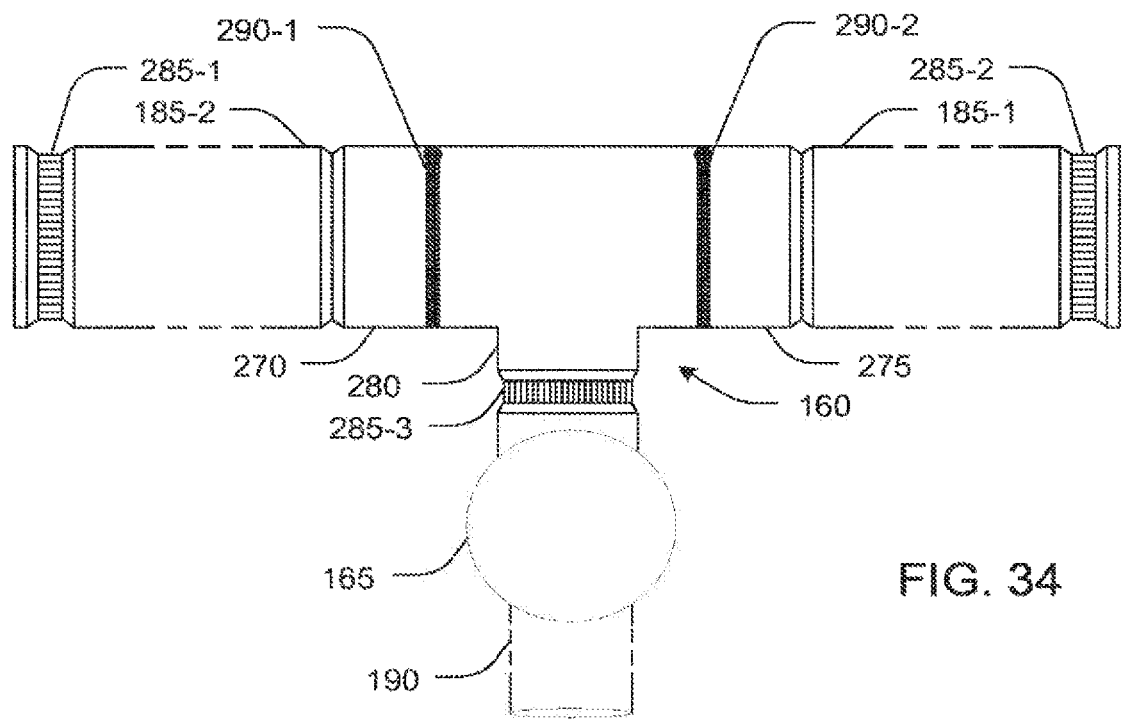
FIG. 34 is a schematic illustrating alternative configuration of the unified airflow assembly of FIG. 33, according to an embodiment of the present disclosure.

In a fourth configuration, as depicted in FIGS. 33-34, the airflow regulator 160 may have a T-shaped, body including a left arm 270, a middle arm 280, and a right arm 275. In one example, the middle arm 280 may be perpendicular to both the left arm 270 and the right arm 275. In another example, the left arm 270 and the right arm 275 may be in the same plane and opposite to each other. In yet another example, each of the left arm 270, the middle arm 280, and the right arm 275 may be in the same plane. In still another example, the middle arm 280 may be in a plane different from that of the left arm 270 and the right arm 275.

The middle arm 280 may extend into the main opening 230, the left arm 270 may extend into the first peripheral opening 235-1, and the right arm 275 may extend into the second peripheral opening 235-2. Each of the main opening 230, the first peripheral opening 235-1, and the second peripheral opening 235-2 may have a substantially circular cross-section: other suitable cross-sectional shapes, e.g., elliptical, oval, polygon, irregular, etc., may be employed based on a cross-section of components being received. Further, as shown in FIG. 33, the middle arm 280 may removably secure the filtration compartment 170, which in turn may be connected or coupled to a portion of the vacuum hose. The left arm 270 may removably secure a filter 285-1, which may be connected or coupled to the accessory hose 185-2. Similarly, the right arm 275 may removably secure a filter 285-2, which may be connected or coupled to a portion of the UV hose 185-1 extending to the head assembly 30 and proximate to the UV lamp 35. Alternatively, as depicted in FIG. 34, the middle arm 280 may directly secure a portion of the vacuum hose, where a filter 285-3 may be removably secured within the vacuum hose instead of being positioned with the middle arm 280. Further, the left arm 270 may directly secure a portion of the accessory hose 185-2, where the filter 285-1 may be removably secured to the accessory hose 185-2. Similarly, the right arm 275 may directly secure a portion of the UV hose 185-1, where the filter 285-2 may be removably secured within the UV hose 185-1.

In such configuration, the T-shaped airflow regulator 160 may include a first air restriction unit 290-1 located adjacent to the left arm 270 and a second air restriction unit 290-2 located adjacent to the right arm 275, such that the middle arm 280 may be located between the first air restriction unit 290-1 and the second air restriction unit 290-2. The first air restriction unit 290-1 may be configured to selectively restrict the airflow through the left arn 270 and the second air restriction unit 290-2 may be configured to selectively restrict the airflow through the right arm 275.

Each of the first air restriction unit 290-1 and the second air restriction unit 290-2 (collectively, referred to as air restriction units 290) may be configured to transition between a closed configuration to an open configuration. In the closed configuration, the air restriction units 290 may move, e.g., substantially perpendicular to a horizontal axis passing through the center of the left arm 270 or the right arm 275, to lock or seal either the left arm 270 and the right arm 275 respectively for restricting the airflow through the locked arm. In the open configuration, the air restriction units 290 and may move away, e.g., substantially parallel to the horizontal axis passing through the center of the left arm 270 or the right arm 275, to open either the left arm 270 and the right arm 275 respectively, thereby allowing the air to pass through the opened arm. One having ordinary skill in the art may implement other possible movements including rotary, pan, swivel, tilt, extend, and slide to maneuver the air restriction units based on the design or structure of the air restriction units.

Accordingly, air restriction units 290 may cause the airflow between the middle arm 280 and the left arm 270 to be mutually exclusive, to the airflow between the middle arm 280 and the right arm 275. In some embodiments, the air restriction units 290 may open the air passage in response to a predetermined temperature being above a predefined threshold value in the T-shaped airflow regulator 160.

The air restriction units 290 may be controlled automatically by the control unit 450 or manually using a variety of mechanisms known in the art, related art, or developed later. Examples of such mechanisms may include, but not limited to, electronic/electrical, mechanical, or electromechanical actuation, or any combination thereof. For example, the first air restriction unit 290-1 may automatically pivot to block the first peripheral opening 235-1 when a human is present proximate to the UVD device 10.

FIGS. 35-42 illustrate exemplary methods of using the unified, airflow system 40 implemented on the UVD device 10 of FIG. 1, according to an embodiment of the present disclosure. The order in which the methods are described is not intended to be construed as a limitation, and any number of the described method steps can be combined or otherwise performed in ally order to implement the methods, or an alternate method. Additionally, individual aspects may be deleted from the method without departing from the spirit and scope of the subject matter described herein. Furthermore, aspects of the methods can be implemented in any suitable hardware, software, firmware, or combination thereof, that exists in the related art or that is later developed.

The methods describe, without limitation, implementation of the UVD device 10 for disinfection and cleaning services scenario. One of skill in the art will understand that the method may be modified appropriately for implementation in a variety of scenarios without departing from the scope and spirit of the disclosure.

Figures 35, 36:
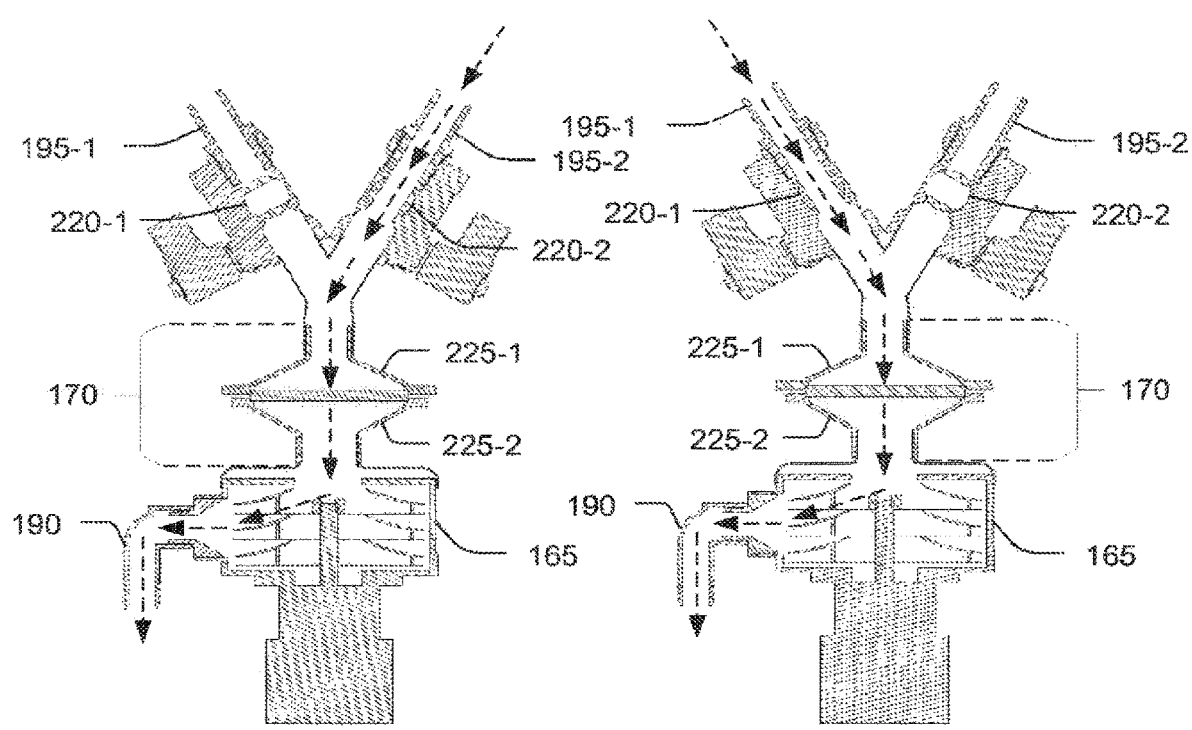
FIGS. 35-36 illustrate an exemplary method of using the unified airflow assembly of FIG. 17 implemented on the UVD device of FIG. 1, according to an embodiment of the present disclosure.
Figure 37:
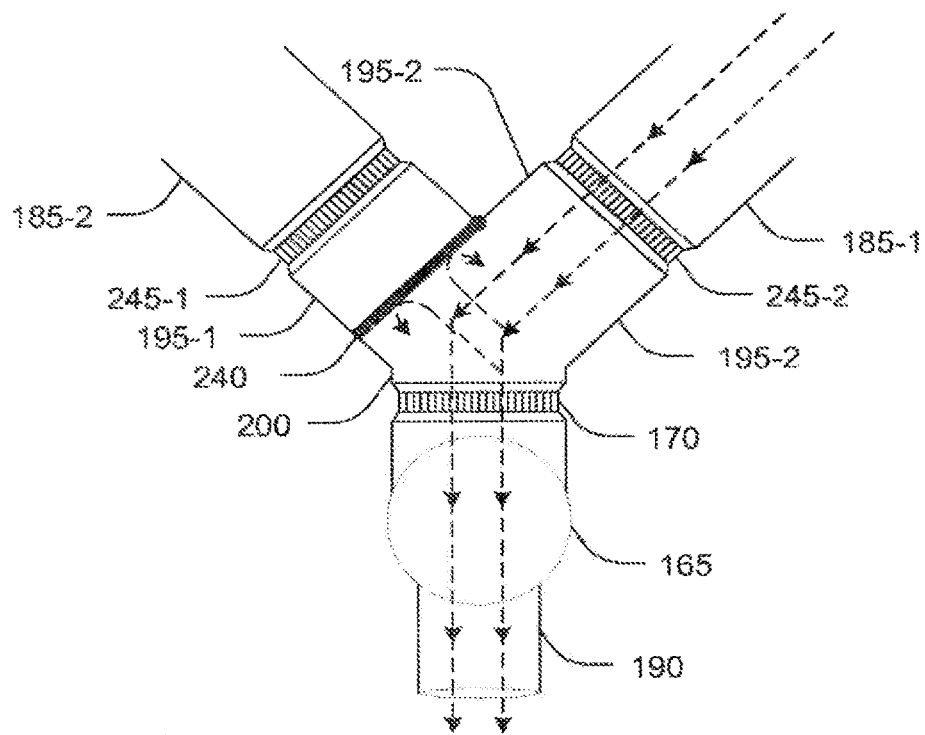
FIGS. 37-38 illustrate an exemplary method of using the unified airflow assembly of FIG. 25 implemented on the UVD device of FIG. 1, according to an embodiment of the present disclosure.
Figure 38:
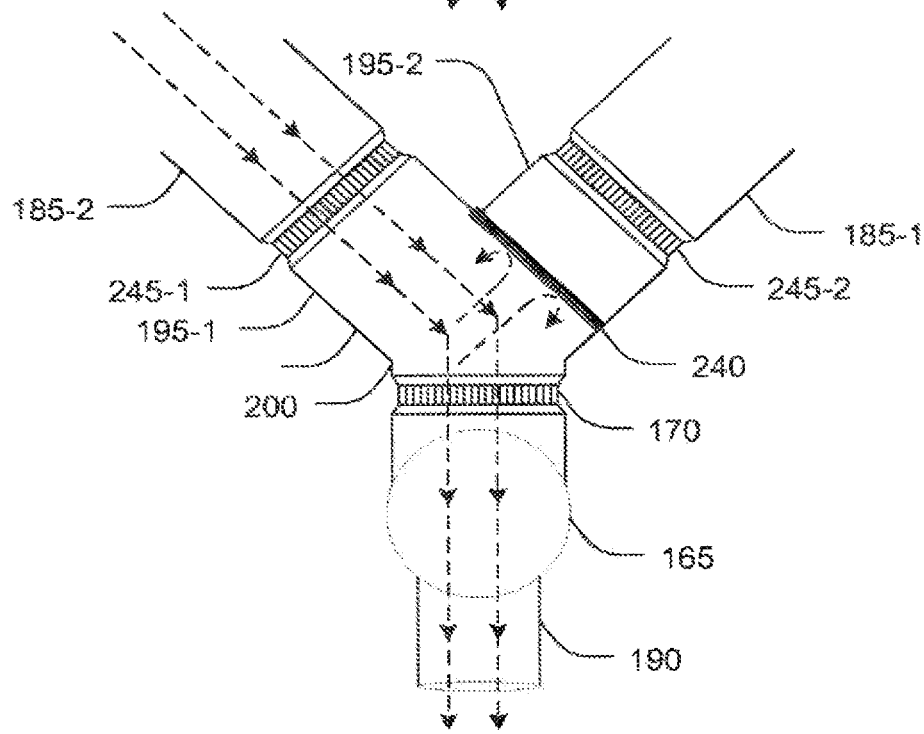
Figure 39:
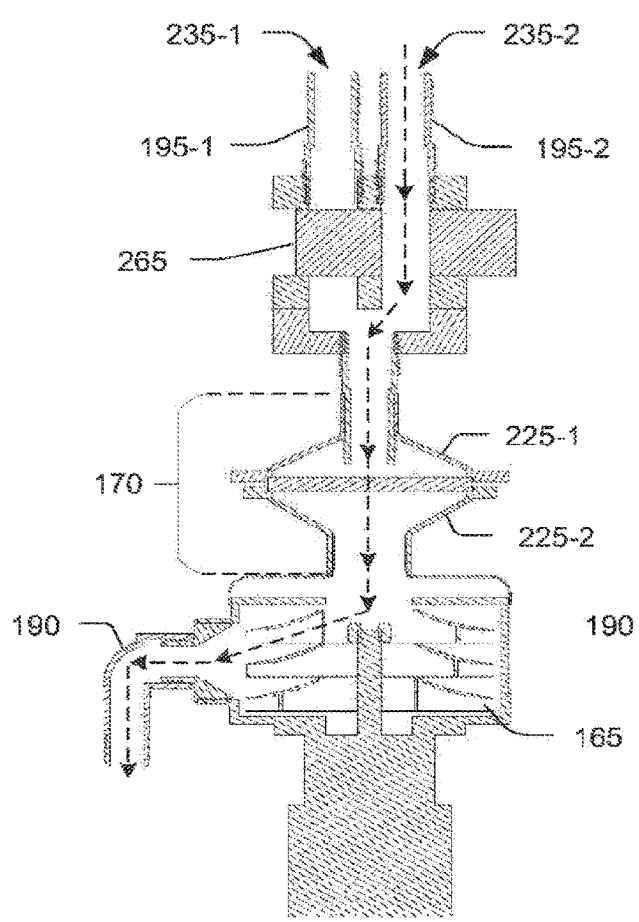
FIGS. 39-40 illustrate an exemplary method of using the unified airflow assembly of FIG. 28 implemented on the UVD device of FIG. 1, according to an embodiment of the present disclosure.
Figure 40:
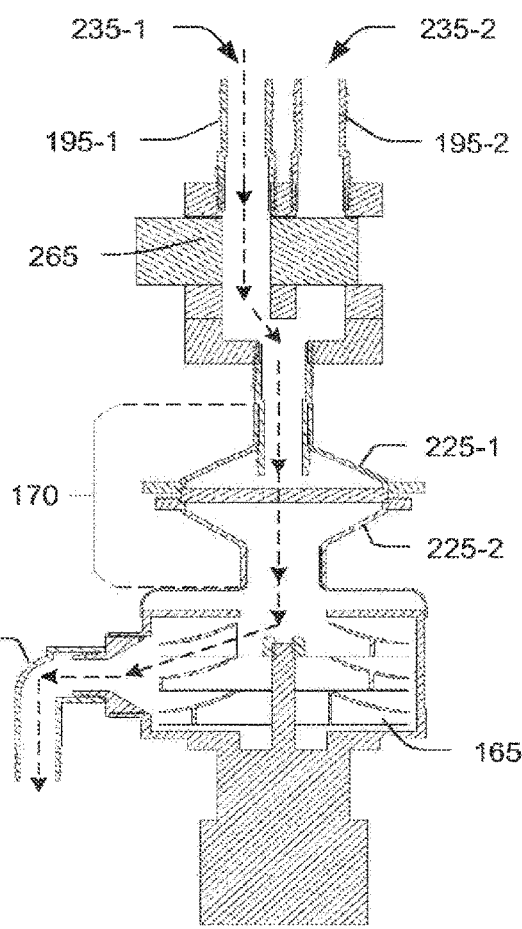
Figure 41:
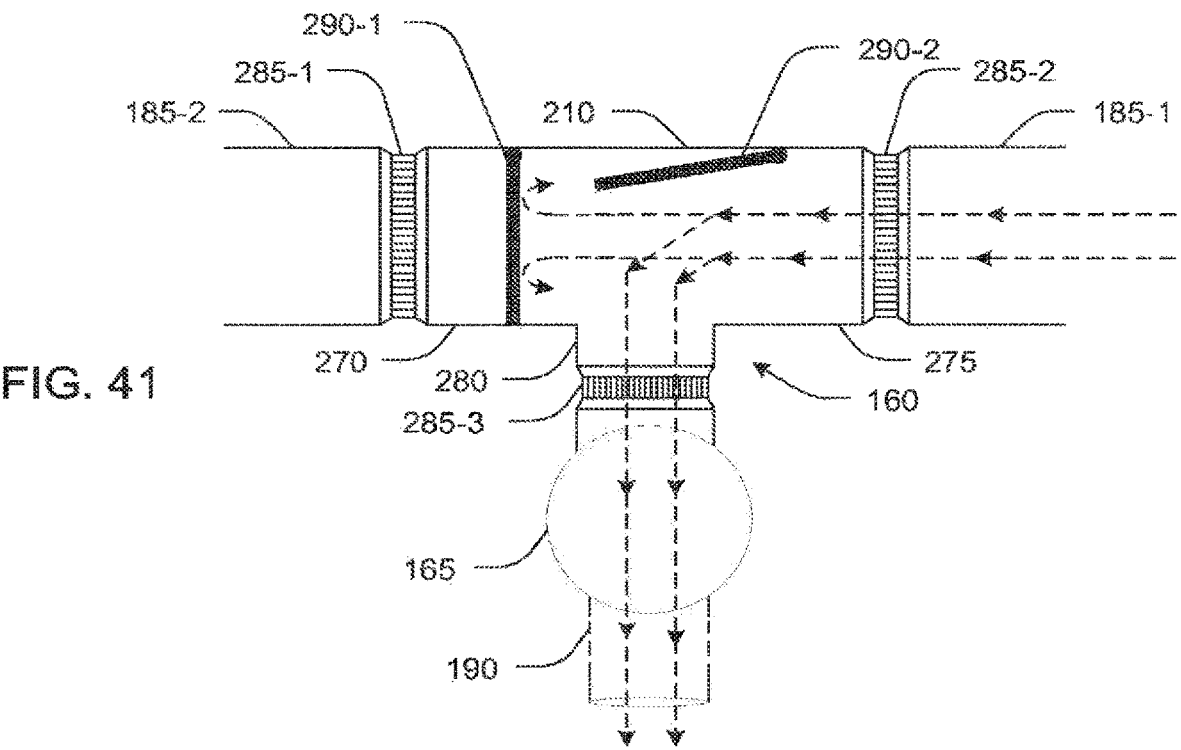
FIGS. 41-42 illustrate an exemplary method of using the unified airflow assembly of FIG. 33 implemented on the UVD device of FIG. 1, according to an embodiment of the present disclosure.
Figure 42:
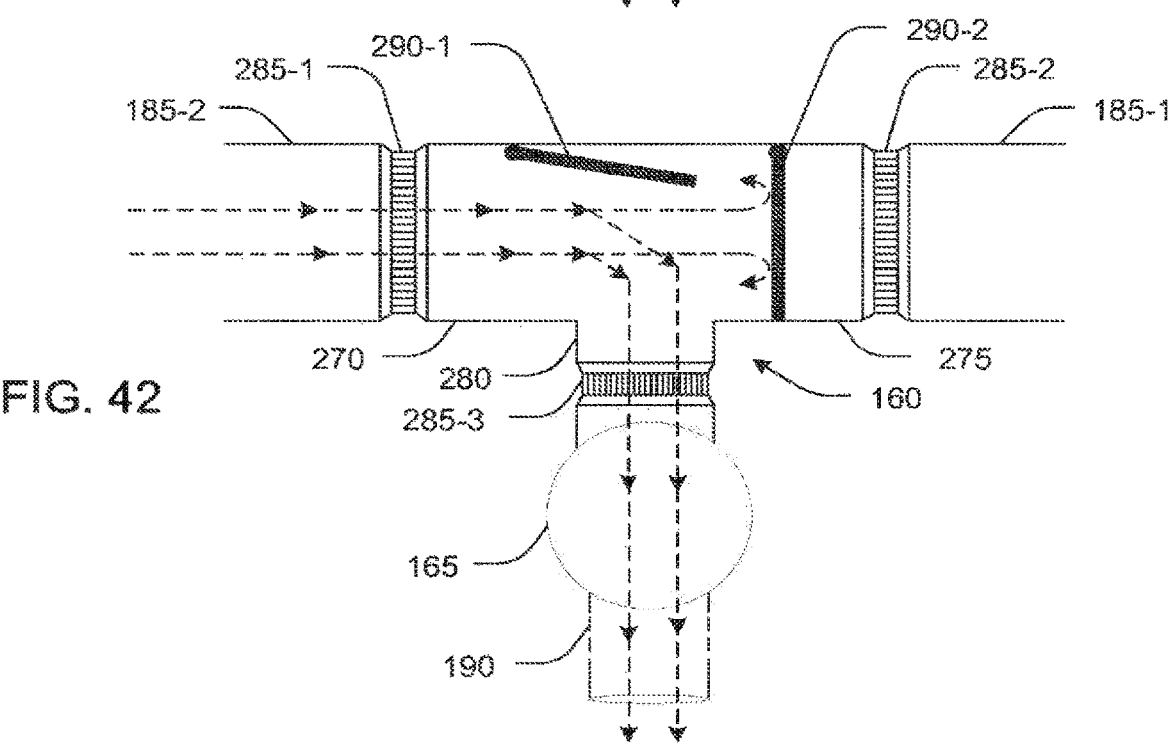

The methods are described with respect to different configurations of the airflow regulator 160 of the unified airflow assembly 145. FIGS. 35-36 illustrate a method with respect to the first configuration of the airflow regulator 160; FIGS. 37-38 illustrates a method with respect to the second configuration: FIGS. 39-40 illustrates a method with respect to the third configuration; and FIGS. 41-42 illustrates a method with respect to the fourth configuration of the airflow regulator 160 discussed above.

The UVD device 10 may be implemented with the unified airflow system 40 and coupled to the airflow accessory 50 configured for decontamination of a target surface. The UVD device 10 may be configured to operate in predetermined modes via the control unit 150. In one embodiment, the UVD device 10 may be configured to operate in a disinfection mode and a cleaning mode, each of which may be implemented in any order; however, an operator may select and perform operations pertaining to the cleaning mode prior to those of the disinfection mode for faster and wholistic decontamination. During operation, an operator may select one of the modes using any of the input devices known in the art, related art, or developed later. For example, the operator may login on an interactive display screen of the display unit 45 in communication with the control unit 150 and select one of those modes on the screen. The control unit 150 may be configured to control the operation of the 12 VD device 10 as well as that of the unified airflow system 40. In some embodiments, the control unit 150 may facilitate the unified airflow system 40 being controlled independent of the UVD device 10. In some other embodiments, each of the unified airflow system 40 and the UVD device 10 may have dedicated control boxes working in synchronization with each other for the intended operation.

Cleaning Mode

When the cleaning mode is selected, the control Unit 150 may deactivate the head assembly 30 including the operation of the UV lamp 35, and allow for activation of the airflow accessory 50, or the cleaning unit 110, coupled to the unified airflow assembly 145 via the first open end 205 of the accessory hose 185-2 secured to the chassis 180. At this point, the control unit 150 may be configured to drive the head assembly 30 in the retracted position or shut down the UV lamp 35 or orient the UV lamp 35 to project towards the UVD device 10, However, in some examples, the control unit 150 may operate to shut down the UV lamp 35 while keeping the head assembly 30 in the open position.

In the first configuration of the airflow regulator 160 (FIG. 36), the control unit 150 may drive the second restriction unit 215-2 in the second side arm 195-2 to selectively restrict an airflow between the vacuum pump 165 and the UV lamp 35 or a site proximate thereto. For example, the control unit 150 may rotate the second solenoid valve 220-2 in the second side arm 195-2 to close the airflow passage therethrough, thereby blocking the airflow passage leading to the UV lamp 35 via the UV hose 185-1 coupled to the second side arm 195-2. However, the first restriction unit 215-1 such as the first solenoid valve 220-1 in the first side arm 195-1 may be maintained in an open position by the control unit 150. As a result, a flow communication may be established between the vacuum pump 165, via the central arm 200, and the airflow accessory 50, or the cleaning unit 110, via the UV hose 185-1 coupled to the first side arm 195-1.

Similarly, in the second configuration of the airflow regulator 160 (FIG. 38), the control unit 150 may drive the air restriction unit 240 to pivot towards the second side arm 195-2 of the Y-shaped airflow regulator 160 while keeping an airflow passage open in the first side arm 195-1. As a result, the airflow passage leading to the UV lamp 35 via the UV hose 185-1 coupled to the first side arm 195-1 may be blocked. However, the airflow passage towards the airflow accessory 50, or the cleaning unit 110, via the accessory hose 185-2 coupled to the first side arm 195-1 may remain open, thereby establishing a flow communication between the vacuum pump 165, via the central arm 200, and the airflow accessory 50, or the cleaning unit 110, via the first side arm 195-1 and the accessory hose 185-2 connected thereto.

Further, in the third configuration of the airflow regulator 160 (FIG. 40), the control unit 150 may drive the air restriction unit such as the linear actuator valve 265, e.g., to the left as shown, for closing the UV arm 255 while aligning the gap 295 in the actuator valve 265 with airflow passage in the accessory arm 250. As a result, the airflow passage in the UV arm 255 may be blocked and that in the accessory arm 250 may be open, thereby establishing a flow communication between the vacuum pump 165, via the central arm 200, and the airflow accessory 50, or the cleaning unit 110, via the accessory arm 250 and the accessory hose 185-2 connected thereto.

In the fourth configuration of the airflow regulator 160 (FIG. 42), the control unit 150 may drive the second air restriction unit 290-2 to extend toward the right arm 275 of the airflow regulator 160. For example, the second air restriction unit 290-2 may be driven to be substantially perpendicular to a horizontal axis passing through the center of the right arm 275, thereby blocking the airflow passage leading to the UV lamp 35 via the UV hose 185-1. As a result, the second air restriction unit 290-2 substantially restricts a flow communication between the vacuum pump 165 and the UV lamp 35 from within the airflow regulator 160. On the other hand, the control unit 150 may pivot the first air restriction unit 290-1 away from the left arm 270 to unblock an air passage that extends to the airflow accessory 50, or the cleaning unit 110, via the left arm 270 of the airflow regulator 160. This unblocked air passage may extend to the airflow accessory 50, or the cleaning unit 110, through the accessory hose 185-2, which, at one end, may be coupled to the airflow accessory 50 directly, or via a distal hose coupled thereto. At the other end, the accessory hose 185-2 may be coupled to the left arm 270. As a result, a flow communication may be established between the accessory hose 185-2, or the cleaning unit 110, and the vacuum pump 165 via the left arm 270.

Subsequently, when the vacuum pump 165 may be activated by the control unit 150, it may create a suction airstream, or a negative air pressure, in the accessory hose 185-2, and by extension in the first set of hoses of the airflow accessory 50 or the second set of hoses of the cleaning unit 110 via the airflow regulator 160. The suction airstream may draw air from the set of proximal hoses, which may accordingly extract contaminants, e.g., from a surface or atmosphere due to the negative air pressure created by the suction airstream. Although the extracted contaminants may be collected in the dirt collection unit 115, the drawn, air may become unclean due such contaminants. This unclean air may be filtered by the filtration unit 120 in the airflow accessory 50, or the cleaning unit 110, as well as the filtration compartment 170 coupled between the airflow regulator 160 and the vacuum pump 165. The filtered air may be expelled from the UVD device 10 through the discharge hose 190 of the vacuum pump 165 via the airflow regulator 160, while the blocked air passage between the vacuum pump 165 and the UV hose 185-1 prevents the unclean air from moving across to the UV lamp 35. Further, the drawn unclean air may be filtered by any additional filters located along the airflow path between the airflow accessory 50, or the cleaning unit 110, and the vacuum pump 165. Accordingly, the proximal hoses may be moved around for removing contaminants from intended surfaces in a designated area using the suction airstream provided by the unified airflow system 40.

Disinfection Mode

After the cleaning operation or when surface disinfection is desired, the operator may deactivate the cleaning mode and remotely select the disinfection mode on the UVD device 10. The operator may devoid, human occupancy in the designated area where the disinfection is to be performed prior to activating the disinfection mode to avoid health hazards due to the UV light.

When the disinfection mode is activated, the control unit 150 may deactivate the airflow accessory 50 and allow for activation of the head assembly 30 and that of the UV lamp 35. At this point, the control unit 150 may be configured to drive the head assembly 30 to the open position from the retracted position. In the open position, the control unit 150 may drive the head assembly 30 out of the recess 60 in the cabinet 20 to a predetermined angle with respect to a horizontal axis substantially parallel to the floor.

In the first configuration of the airflow regulator 160 (FIG. 35), the control unit 150 may drive the first restriction unit 215-1 in the first side arm 195-1 to selectively restrict an airflow between the vacuum pump 165 and the airflow accessory 50, or the cleaning unit 110. For example, the control unit 150 may rotate the first solenoid valve 220-1 in the first side arm 195-1 to close the airflow passage therethrough, thereby blocking the airflow passage leading to the airflow accessory 50, or the cleaning unit 110, via the accessory hose 185-2. However, the second restriction unit 215-2 such as the second solenoid valve 220-2 in the second side arm 195-2 may be maintained in an open, position by the control, unit 150. As a result, a flow communication may be established between the vacuum pump 165, via the central arm 200, and the UV lamp 35 via the UV hose 185-1 coupled to the second side arm 195-2.

Similarly, in the second configuration of the airflow regulator 160 (FIG. 37), the control unit 150 may drive the air restriction unit 240 to pivot towards the first side arm 195-1 of the Y-shaped airflow regulator 160 while keeping an airflow passage open in the second side arm 195-2. As a result, the airflow passage leading to the airflow accessory 50, or the cleaning unit. 110, via the accessory hose 185-2 coupled to the first side arm 195-1 may be blocked. However, the airflow passage towards the UV lamp 35 via the UV hose 185-1 coupled to the second side arm 195-2 may remain open, thereby establishing a flow communication between the vacuum pump 165, via the central arm 200, and the UV lamp 35 via the second side arm 195-2 and the UV hose 185-1 connected thereto.

Further, in the third configuration of the airflow regulator 160 (FIG. 39), the control unit 150 may drive the air restriction unit such as the linear actuator valve 265, e.g., to the right as shown, for closing the accessory arm 250 while aligning the gap 295 in the actuator valve 265 with airflow passage in the UV arm 255. As a result, the airflow passage in the accessory arm 250 may be blocked and that in the UV arm 255 may be open, thereby establishing a flow communication between the vacuum pump 165, via the central arm 200, and the UV lamp 35 via the UV arm 255 and the UV hose 185-1 connected thereto.

In the fourth configuration of the airflow regulator 160 (FIG. 41), the control unit 150 may drive the first air restriction unit 290-1 to extend toward the left arm 270 of the airflow regulator 160. For example, the first air restriction unit 290-1 may be driven to be substantially perpendicular to a horizontal axis passing through the center of the left arm 270, thereby blocking the airflow passage leading to the airflow accessory 50 via the accessory hose 185-2. As a result, the first air restriction unit 290-1 substantially restricts a flow communication between the vacuum pump 165 and the airflow accessory 50, or the cleaning unit 110, from within the airflow regulator 160. On the other hand, the control unit 150 may pivot the second air restriction unit 290-2 away from the right arm 275 to unblock an air passage that extends to the UV lamp 35 via the right arm 275 of the airflow regulator 160. This unblocked air passage may extend to the UV lamp 35 through the UV hose 185-1, which, at one end, may be proximate to the UV lamp 35 in the head assembly 30 and at the other end, may be coupled to the right arm 275. As a result, a flow communication may be established between the UV lamp 35 and the vacuum pump 165 via the right arm 275.

Subsequently, upon being switched on by the control unit 150, e.g., based on an input received from an operator, the vacuum pump 165 may create a suction airstream, or a negative air pressure, in the UV hose 185-1. The suction airstream may draw the hot air proximate to the UV lamp 35 via the UV hose 185-1, thereby cooling the UV lamp 35. The drawn hot air may be expelled through the discharge hose 190 of the vacuum pump 165 via the airflow regulator 160 while the respective air restriction units 215-1, 220-1, 240, 265, 290-1 blocking the air passage to the airflow accessory 50 may prevent the unclean air or any residue in the accessory hose 185-2 coupled to the airflow accessory 50, or the cleaning unit 110, from moving across to the UV lamp 35. Further, the hot air drawn from the UV lamp 35 may contain ozone, which may be filtered by one or more filters such as the gas filter 175 coupled to the discharge hose 190 along the airflow passage between the UV lamp 35 and the vacuum pump 165, thereby preventing any health hazards.

While being cooled by the suction airstream, the control unit 150 may orient the head assembly 30 at predetermined angles for the UV lamp 35 to project the UV light on intended surfaces such floor, walls, ceilings, and objects in a designated area. The UV light may disinfect the surfaces, which were previously decontaminated during the cleaning mode, for a wholistic and faster decontamination. The disinfection mode may be activated for a predefined or dynamically defined duration and may be interrupted either on-demand by the operator or based on preset or dynamically set conditions such as those indicated by various sensors (e.g., motion/vibration sensors, occupancy/proximity sensors, ozone sensors, temperature sensors, smoke sensors, pathogen level detection sensors, etc.) in communication with the UVD device 10. Examples of these conditions may include, but not limited to, motion detection in the proximity of the UVD device 10 or remote sensors communicating therewith, temperature of the UV lamp above a predefined threshold, accumulation of ozone above a predefined threshold, and so on.

The above description does not provide specific details of manufacture or design of the various components. Those of skill in the art are familiar with such details, and unless departures from those techniques are set out, techniques, known, related art or later developed designs and materials should be employed. Those in the art are capable of choosing suitable manufacturing and design details. Notably, the figures and examples described herein are not meant to limit the scope of the present disclosure to a single embodiment, but other embodiments are possible by way of interchange of some or all of the described or illustrated elements.

The terminology used herein is for the purpose of describing particular embodiments only and is not intended to be limiting of the disclosure. It will be appreciated that several of the above-disclosed and other features and functions, or alternatives thereof, may be combined into other systems or applications. Various presently unforeseen or unanticipated alternatives, modifications, variations, or improvements therein may subsequently be made by those skilled in the art without departing from the scope of the present disclosure as encompassed by the following claims.

What is claimed is:

1. A system for surface disinfection, the system comprising:
    a device comprising an ultraviolet (UV) source configured to project UV light on to a target surface;
    an airflow accessory configured to remove contaminants from the target surface using an airstream; and
    a control unit configured to drive at least one air restriction unit for directing the airstream to only one of the UV source and the airflow accessory, wherein the control unit manipulates a portion of the device and the at least one air restriction unit based on a predetermined operational mode, wherein the portion contains the UV source.

2. The system of claim 1, wherein the predetermined operational mode includes at least one of a disinfection mode and a cleaning mode, wherein the control unit is further configured to:
    in the cleaning mode,
        manipulate the portion or the UV source to prevent the UV light from being projected exterior to the device, and
        drive the at least one air restriction unit to direct the airstream to the airflow accessory, and
    in the disinfection mode,
        drive the at least one air restriction unit to direct the airstream to the UV source, and
        manipulate the portion or the UV source to project the UV light exterior to the device to the target surface.

3. The system of claim 2, wherein the control unit is configured to further manipulate the portion or the UV source in the disinfection mode to interrupt the UV light based on at least one of a motion being detected proximate to the device or a sensor communicating therewith, a change in temperature of the UV source relative to a predefined threshold, and an accumulation of ozone proximate to the device above a preset threshold.

4. The system of claim 1, further comprising an airflow source providing the airstream.

5. The system of claim 4, wherein the airflow source includes a vacuum pump configured to create a negative pressure in the airstream.

6. The system of claim 1, wherein the portion or the UV source is manipulated to a recessed arrangement where the UV light is prevented from being projected exterior to the device.

7. The system of claim 1, wherein the device further comprises an additional UV source placed along an outer surface of the device.

8. The system of claim 1, wherein the target surface includes one or more surfaces.

9. The system of claim 1, wherein the airflow accessory includes a handheld portion or a wearable portion.

10. The system of claim 1, wherein the airflow accessory is configured to remove the contaminants using the airstream in combination with a cleaning agent including at least one of a chemical agent, a physical agent, and a biological agent.

11. A method for surface disinfection, the method comprising:
    providing a device comprising an ultraviolet (UV) source configured to project UV light towards a target surface and an airflow accessory configured to remove contaminants from the target surface using an airstream;
    driving, using a control unit, at least one air restriction unit for directing the airstream to only one of the UV source and the airflow accessory; and
    manipulating, using the control unit, a portion of the device and the at least one air restriction unit based on a predetermined operational mode, wherein the portion contains the UV source.

12. The method of claim 11, wherein the predetermined operational mode includes at least one of a disinfection mode and a cleaning mode, wherein the step of manipulating further includes:
    in the cleaning mode,
        manipulating, using the control unit, the portion or the UV source to prevent the UV light from being projected exterior to the device, and
        driving, using the control unit, the at least one air restriction unit to direct the airstream to the airflow accessory, and
    in the disinfection mode,
        driving, using the control unit, the at least one air restriction unit to direct the airstream to the UV source, and
        manipulating, using the control unit, the portion or the UV source to project the UV light exterior to the device to the target surface.

13. The method of claim 12, wherein the step of manipulating in the disinfection mode further includes manipulating, using the control unit, the portion or the UV source to interrupt the UV light based on at least one of a motion being detected proximate to the device or a sensor communicating therewith, a change in temperature of the UV source relative to a predefined threshold, and an accumulation of ozone proximate to the device above a preset threshold.

14. The method of claim 11, further comprising providing the airstream from an airflow source.

15. The method of claim 14, wherein the airflow source includes a vacuum pump configured to create a negative pressure in the airstream.

16. The method of claim 11, wherein the portion or the UV source is manipulated to a recessed arrangement where the UV light is prevented from being projected exterior to the device.

17. The method of claim 11, wherein the device further comprises an additional UV source placed along an outer surface of the device.

18. The method of claim 11, wherein the target surface includes one or more surfaces.

19. The method of claim 11, wherein the airflow accessory includes a handheld portion or a wearable portion.

20. The method of claim 11, further comprising removing the contaminants by the airflow accessory using the airstream in combination with a cleaning agent including at least one of a chemical agent, a physical agent, and a biological agent.

\* \* \* \* \*